(12) United States Patent  
Kitagawa et al.

(10) Patent No.: US 9,068,964 B2
(45) Date of Patent: Jun. 30, 2015

(54) BLOOD CELL COUNTER AND CELL COUNTING METHOD

(71) Applicant: Sysmex Corporation, Kobe-shi (JP)

(72) Inventors: Nobuhiro Kitagawa, Kobe (JP); Masahiko Oguro, Kobe (JP); Kozo Fujii, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 252 days.

(21) Appl. No.: 13/679,201

(22) Filed: Nov. 16, 2012

(65) Prior Publication Data

US 2013/0125628 A1 May 23, 2013

(30) Foreign Application Priority Data

Nov. 18, 2011 (JP) ................................. 2011-253290

(51) Int. Cl.
*G01N 33/49* (2006.01)
*G01N 35/10* (2006.01)
*G01N 15/10* (2006.01)
*G01N 35/00* (2006.01)

(52) U.S. Cl.
CPC ............ *G01N 33/49* (2013.01); *G01N 33/4915* (2013.01); *G01N 35/1079* (2013.01); *G01N 2015/1006* (2013.01); *G01N 2035/00524* (2013.01)

(58) Field of Classification Search
CPC .............. G01N 33/49; G01N 35/1079; G01N 2035/00524; G01N 33/4915; G01N 2015/1006; G01N 35/026; G01N 35/04; B01F 11/0008; B01F 11/0017
USPC ......... 73/61.41, 61.48; 436/520, 807; 422/44, 422/63, 68.1, 73, 509, 512, 520, 550, 561, 422/100, 99; 435/2
See application file for complete search history.

(56) References Cited

U.S. PATENT DOCUMENTS

| 4,518,264 | A | * | 5/1985 | Nohso ........................... 366/208 |
| 6,818,182 | B2 | | 11/2004 | Le Comte et al. |
| 7,485,258 | B2 | * | 2/2009 | Burger et al. .................... 422/22 |
| 2008/0053201 | A1 | * | 3/2008 | Roesicke et al. ............. 73/61.41 |
| 2011/0076668 | A1 | * | 3/2011 | Oguro .............................. 435/2 |
| 2012/0170020 | A1 | * | 7/2012 | Bado et al. ....................... 356/39 |

FOREIGN PATENT DOCUMENTS

JP 09-015113 A 1/1997

* cited by examiner

*Primary Examiner* — Daniel S Larkin
(74) *Attorney, Agent, or Firm* — Brinks Gilson & Lione

(57) ABSTRACT

A blood cell counter comprises a stirrer which stirs a whole blood sample in a sample container by moving the sample container, an aspirator which aspirates the whole blood sample by penetrating a lid of the sample container with an aspiration tube after stirring by the stirrer, a detector which counts the blood cells in the whole blood sample aspirated by the aspirator, and a force applying member which applies a force to the sample container in an upright state after stirring by the stirrer so as to remove the whole blood sample from the lid of the sample container.

20 Claims, 17 Drawing Sheets

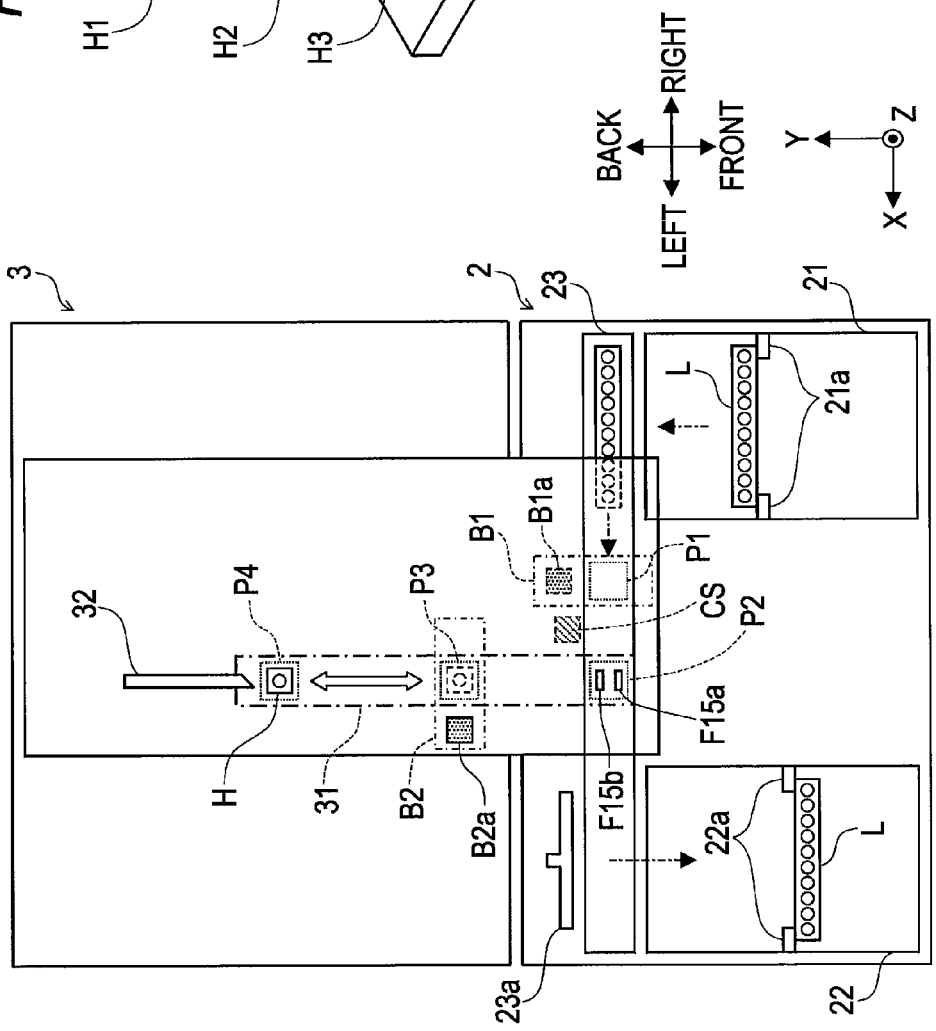

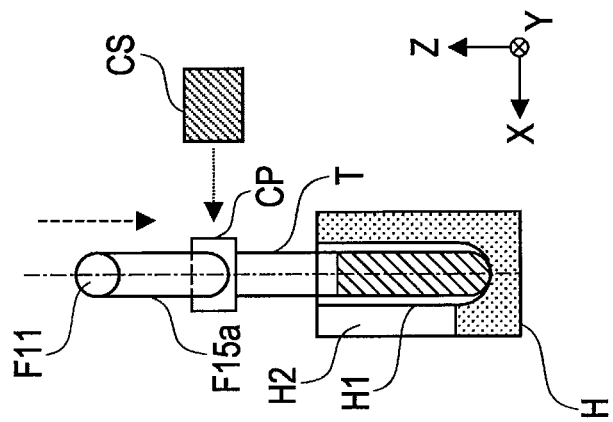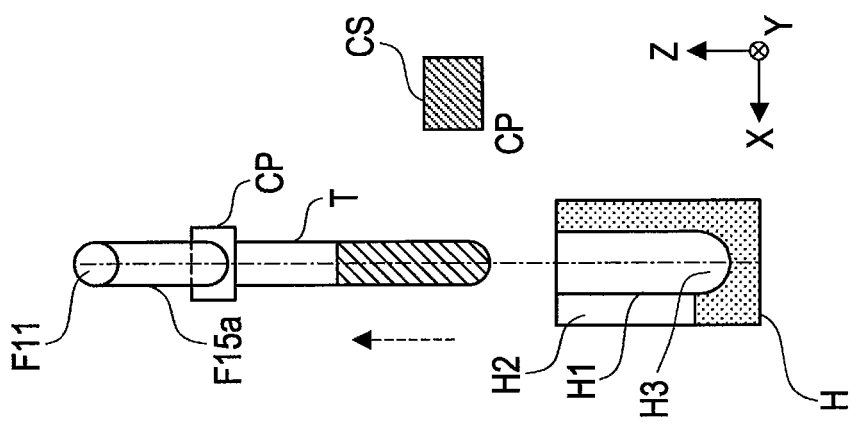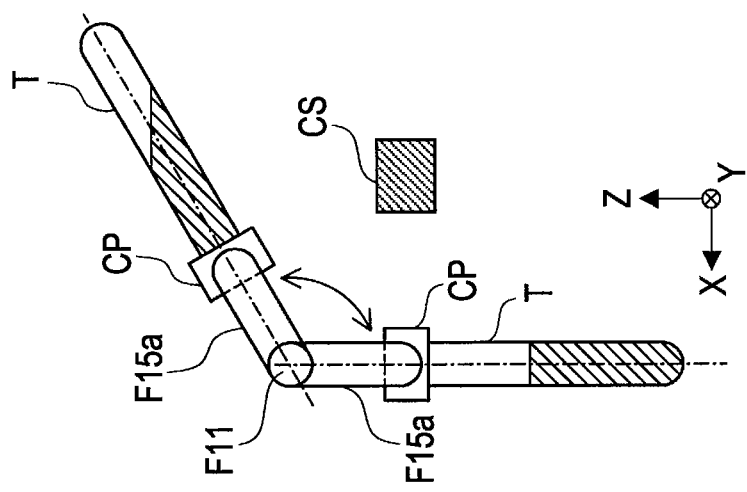

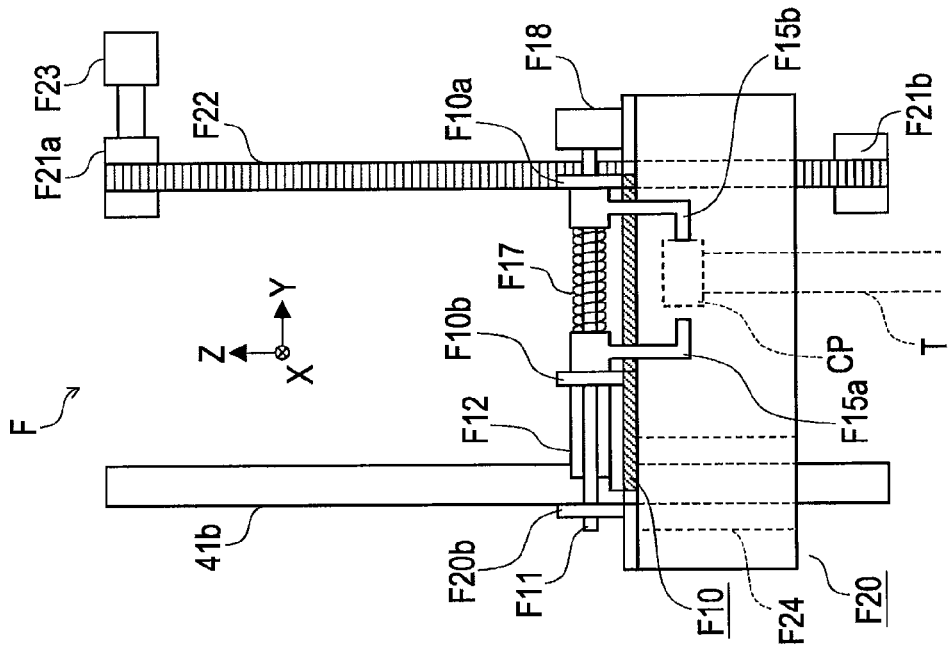
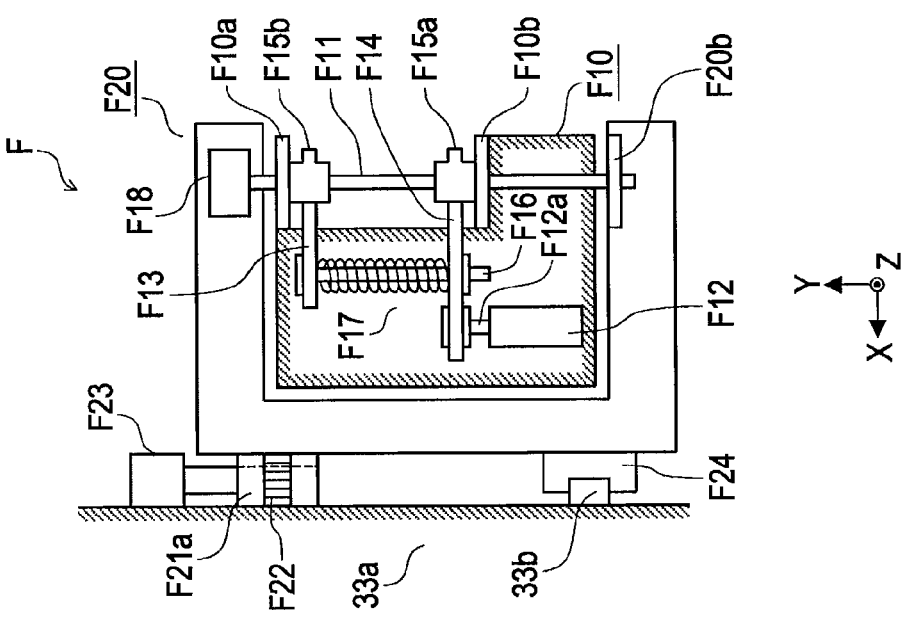

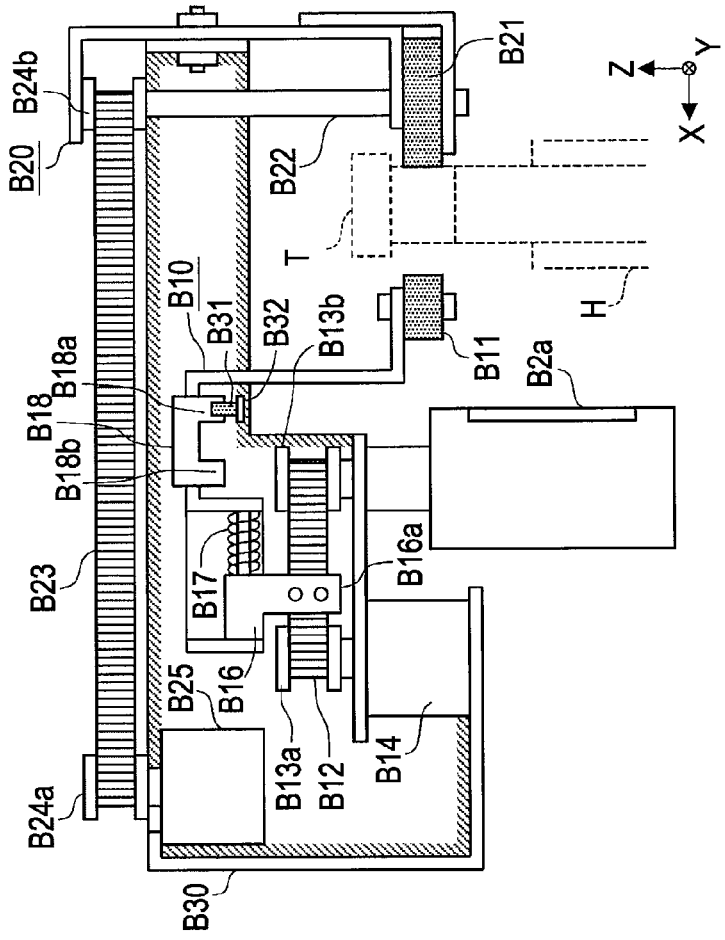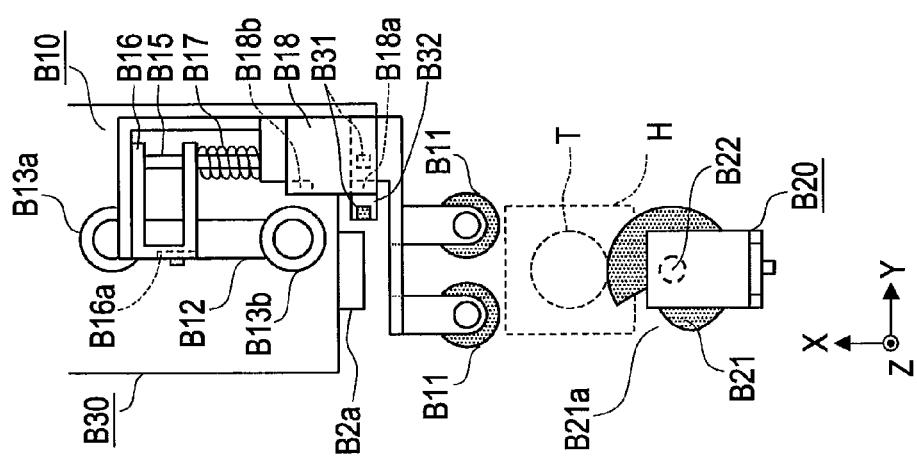

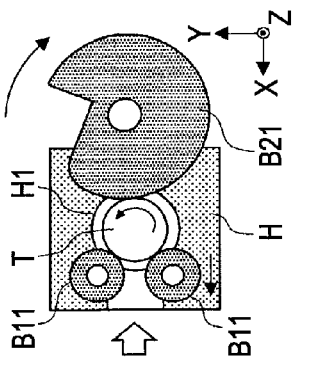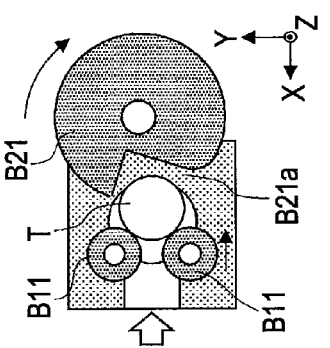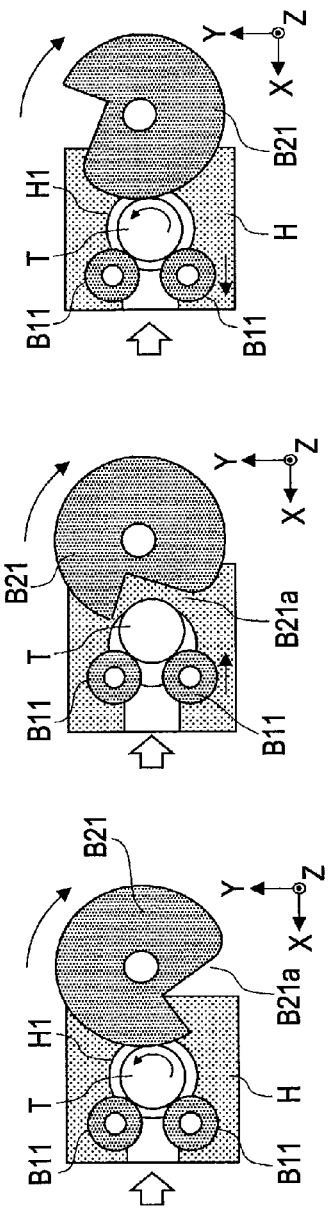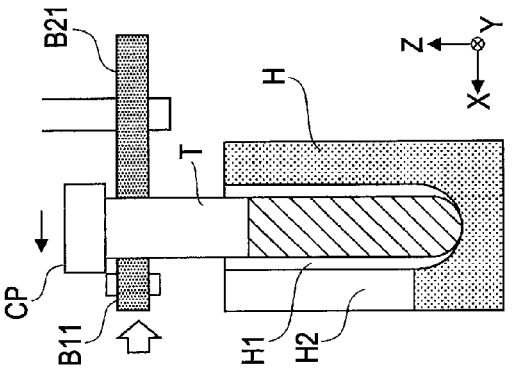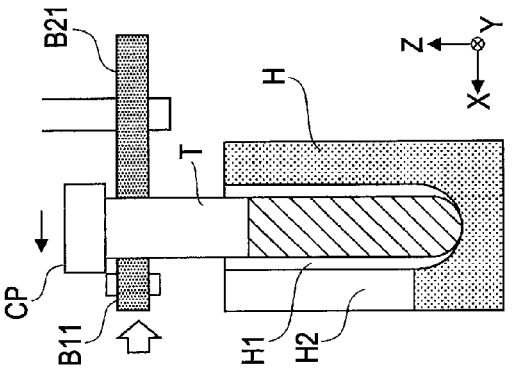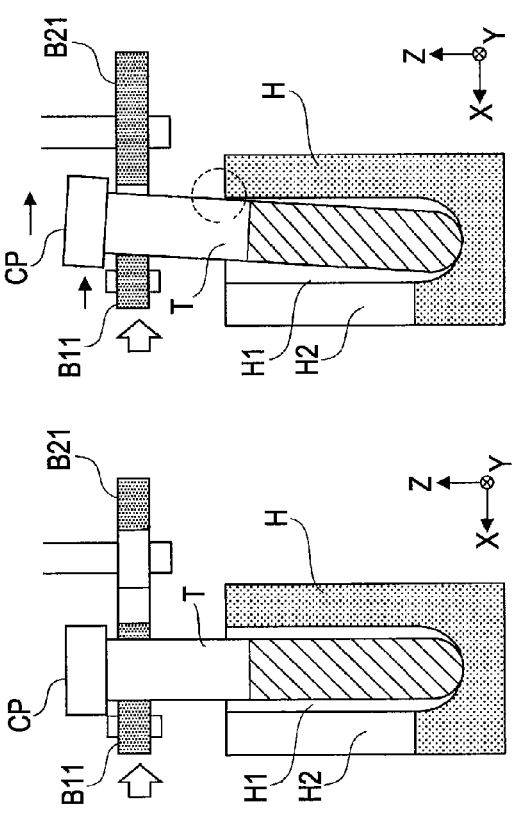

BLOOD CELL COUNTER AND CELL COUNTING METHOD

RELATED APPLICATIONS

This application claims priority under 35 U.S.C. §119 to Japanese Patent Application No. 2011-253290 filed on Nov. 18, 2011, the entire content of which is hereby incorporated by reference.

BACKGROUND OF THE INVENTION

1. Field of the Invention

The present invention relates to a blood cell counting apparatus and a blood cell counting method for counting blood cells contained in a whole blood sample.

2. Description of the Related Art

Conventional blood cell counting apparatuses are known wherein an aspirating tube is passed through a cap that seals a sample container which contains a whole blood sample to aspirate the whole blood sample from the sample container, and the blood cells contained in the aspirated whole blood sample are then counted. The sample container must be stirred to equalize the concentration of the whole blood sample in the sample container before the whole blood sample is aspirated since the blood cell components contained in the whole blood sample will settle when allowed to stand. In this case, the agitation of the sample container may be performed manually by the user, or mechanically by the cell counting apparatus via a mechanism to perform agitation disposed within the cell counting apparatus.

U.S. Pat. No. 6,818,182 discloses an apparatus provided with a mechanism for stirring a sample container containing a whole blood sample. This apparatus has a shaft disposed horizontally, a rotating head capable of rotation in the circumferential direction of the shafts, and a pick-up device disposed at the tip of the rotating head for grasping both sides of a sample container. The apparatus grasps the midsection of the upright sample container via the pick-up device, rotates the rotating head 360 degrees in the circumferential direction relative to the shaft, to complete one rotation of the sample container pivoting on the grasped section, hence stirring the whole blood within the sample container.

When stirring the whole blood sample by the aforesaid method, however, part of the whole blood sample remains inside the cap of the sample container. When the cap is pierced by the aspirating tube while in this condition, the whole blood adhered inside the cap may be emitted to the outside.

SUMMARY OF THE INVENTION

The scope of the present invention is defined solely by the appended claims, and is not affected to any degree by the statements within this summary.

A first aspect of the present invention is a blood cell counter comprising:

a stirrer which stirs a whole blood sample in a sample container by moving the sample container;

an aspirator which aspirates the whole blood sample by penetrating a lid of the sample container with an aspiration tube after stirring by the stirrer;

a detector which counts the blood cells in the whole blood sample aspirated by the aspirator; and a force applying member which applies a force to the sample container in an upright state after stirring by the stirrer so as to remove the whole blood sample from the lid of the sample container.

A second aspect of the present invention is a blood cell counter comprising:

a sample aspirator which pierces a lid of a sample container with an aspirating tube and aspirates a whole blood sample in the sample container;

a detector which counts the blood cells in the whole blood sample aspirated by the aspirator; and a force applying member which applies a force to the sample container in an upright state so as to remove the whole blood sample from the lid of the sample container before aspiration by the sample aspirator.

A third aspect of the present invention is a cell counting method, comprising:

stirring a whole blood sample in a sample container by moving the sample container;

applying the force to a sample container while the sample container is upright to remove whole blood sample attached to the lid of the sample container from the lid;

piercing the lid of the sample container with an aspirating tube and aspirating the whole blood sample from the sample container; and counting the blood cells contained in the whole blood sample.

BRIEF DESCRIPTION OF THE DRAWINGS

FIG. 3A is a plan view showing the structures of the transporting unit and measurement unit of the embodiment viewed from above, and FIG. 3B schematically shows the structure of the sample container holder;

FIGS. 4A, 4B, and 4C schematically show the mixing operation of the sample container, the operation of setting the sample container in the sample container holder, and the detection operation of the specific cap of the embodiment;

FIGS. 5A and 5B show the structure of the holding unit of the embodiment;

FIGS. 6A and 6B show the structure of the barcode unit of the embodiment;

FIGS. 7A-7F show the operation of the barcode unit of the embodiment;

DETAILED DESCRIPTION OF THE PREFERRED EMBODIMENTS

Figure 1:
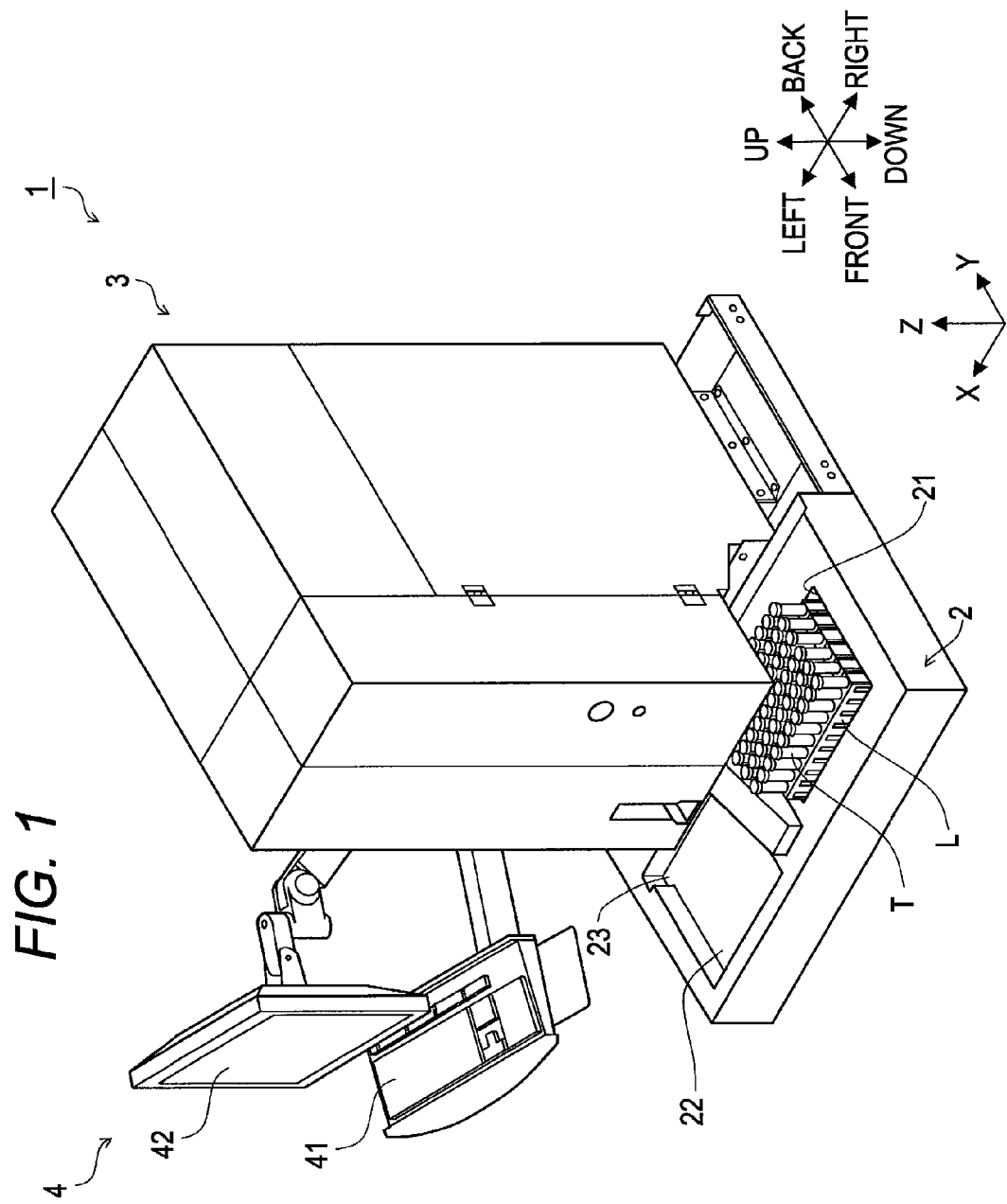
FIG. 1 is a perspective view showing an external view of an embodiment of a blood cell counting apparatus.

The preferred embodiments of the present invention will be described hereinafter with reference to the drawings.

The present embodiment applies the present invention to a blood cell counting apparatus for counting blood cells contained in whole blood samples.

The blood cell counting apparatus of the embodiment is described below referring to the drawings.

FIG. 1 is an exterior view showing the general structure of an a blood counting apparatus 1. The blood counting apparatus 1 of the present embodiment is configured by a transporting unit 2, measurement unit 3, and information processing unit 4.

The transporting unit 2 is disposed in front of the measurement unit 3, and is configured by a right table 21, left table 22, and a rack transporter 23 connecting the right table 21 and the left table 22. The right table 21 and the left table 22 can accommodate ten sample racks L that have a holding part.

Figure 2C:
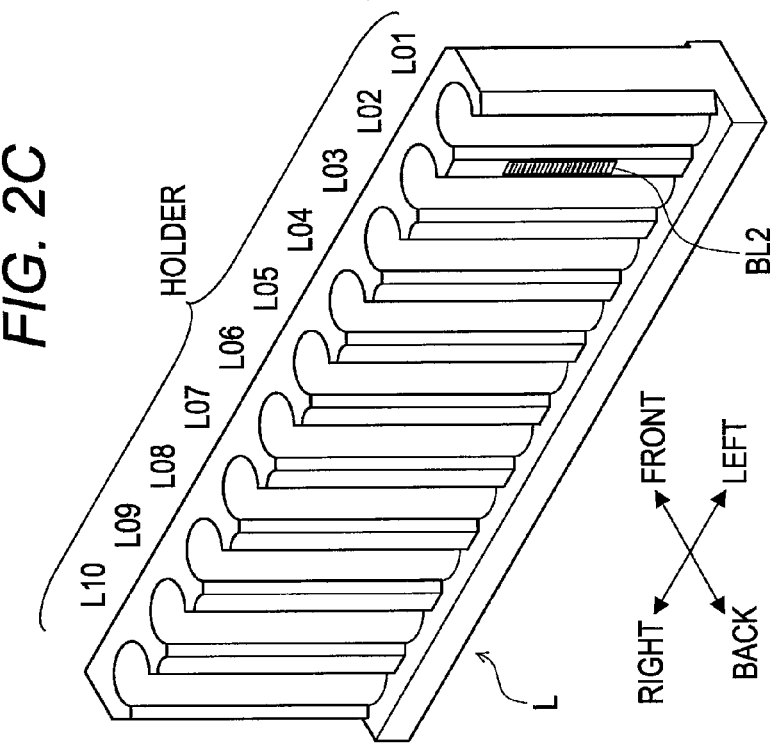
FIGS. 2A, 2B, and 2C show the structures of a sample container, a cap for sealing the sample container, and a sample rack of the embodiment.
Figure 2A:
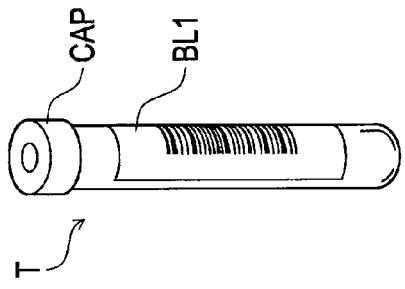
Figure 2B:
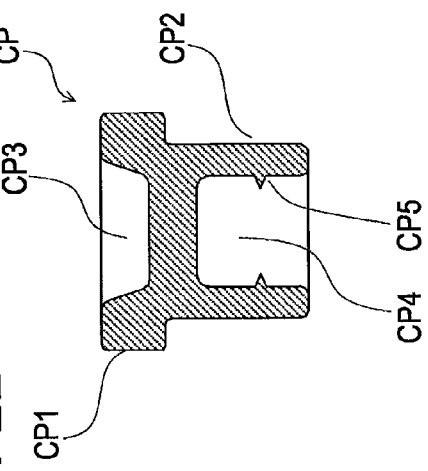

FIG. 2A through C respectively show the structures of the sample container T, rubber cap CP, and sample rack L.

Referring to FIG. 2A, the sample container T is a tube-like container, open at the top end, formed of transparent synthetic resin or glass. A barcode label BL1 is adhered to the outside surface of the sample container T. A barcode that includes the sample ID identifying the individual sample is printed on the barcode label BL1. The sample container T contains a whole blood sample collected from a patient, and the opening at the top end is sealed by a rubber cap that can be pierced by a piercer 32 to be described later.

FIG. 2B shows an example of a cap. FIG. 2B shows a cross section when the cap is cut at a plane passing through the center axis of the cap.

Referring to FIG. 2B, the example of the cap CP has a cylindrical head part CP1 and a cylindrical body part CP2. A circular concavity CP3 is formed on the top surface of the head part CP1, and a cylindrical concavity CP4 is formed on the bottom surface of the body part CP2. A ring-like protrusion CP5 is also formed at a predetermined depth position on the inner surface of the concavity CP4. The cap CP has a symmetrical configuration relative to the center axis.

As shown in FIG. 2B, the cap CP is configured so that the depth of the concavity CP4 is sufficient to accommodate the ring-like protrusion CP5 set at a predetermined depth. Hence, when the cap CP is used to seal the sample container T, the whole blood sample readily remains on the inner side of the cap, that is, in the bottom of the concavity CP4, after the agitation operation which is described later.

A cap other than the cap CP shown in FIG. 2B may be used to seal the sample container T. A cap other than the cap CP may have a wider width and shallower concavity on the inner side, such that the shape may make it difficult to retain the whole blood sample on the inner side of the cap compared to the cap CP. Note that the cap CP shown in FIG. 2B has a milk-white color to make it distinguishable from other caps by color. The cap CP shown in FIG. 2B is hereinafter referred to as "specific cap CP."

Referring to FIG. 2C, supporters L01 through L10 are formed on the sample rack L, and are capable of holding sample containers T in a perpendicular position. The barcode label BL2 is adhered to the side surface on the back of the sample rack L. A barcode indicating the rack ID is printed on the barcode label BL2.

Returning to FIG. 1, the transporting unit 2 accommodates a sample rack L placed on the right table 21 by the user. The transporting unit 2 transports the sample rack L held on the right table 21 to a predetermined position of the rack transporter 23 to supply the sample containers T to the measurement unit 3. The transporting unit 2 then transports the sample rack L on the rack transporter 23 to the left table 22.

When the sample container T is positioned at the predetermined position of the rack transporter 23, the measurement unit 3 removes the sample container T from the sample rack L by the hands 15a and 15b, to move the sample container T to the measurement unit 3. The measurement unit 3 measures the whole blood sample in the sample container T while the sample container T is inside the measurement unit 3, and counts the blood cells contained in the whole blood sample. When the measurement is completed, the measurement unit 3 returns the sample container T back to the original sample rack L.

The information processing unit 4 has an input part 41 and a display part 42. The information processing unit 4 is connected via a communication network so as to be capable of communicating with the transporting unit 2, measurement unit 3, and a host computer (not shown). The information processing unit 4 controls the operation of the transporting unit 2 and the measurement unit 3, performs analysis based on the measurement results of the measurement unit 3, and transmits the analysis results to the host computer.

FIG. 3 is a plan view showing the structures of the transporting unit 2 and the measurement unit 3 when viewed from above. Note that although various sensors for detecting the sample rack L and the sample container T are disposed at predetermined positions on the right table 21, left table 22, and the rack transporter 23, these sensors are omitted from the drawings.

A rack take-up device 21a is provided on the right table 21 to deliver the sample rack L to the right end position of the rack transporter 23. A barcode unit B1 is also provided at a reading position P1 on the transport path of the rack transporter 23; the barcode unit B1 includes a barcode reader B1a for reading the barcode label BL1 of the sample container T. Hand parts F15a and F15b for grasping the sample container T from above the sample rack L are provided at a take-up position P2 on the transport path of the rack transporter 23. The hand parts F15a and F15b grip the head (cap) of the sample container T in front and back directions, remove the sample container T upward, and oscillate the grasped sample container T in lateral directions. Hence, the whole blood sample within the sample container T is stirred.

Note that the hand parts F15a and F15b are constructed as part of a holding unit F to be described later. The structure of the holding unit F is described later pursuant with FIG. 5.

A color sensor unit CS is provided near the take-up position P2, and detects whether the cap installed on the sample container T is a specific cap CP. The color sensor unit CS is provided with a white light source for emitting white light, and a color sensor. The white light source irradiates a white light from between the hand parts F15a and F15b holding the cap onto the cap. The color sensor detects the color of the cap irradiated by the white light from between the hand parts F15a and F15b, and outputs data representing the brightness level of red, blue, green color.

A sample container transporter 31 is provided in the measurement unit 3 to move the sample container T held by the hand parts F15a and F15b into the measurement unit 3. The sample container transporter 31 is provided with a sample container holder H, and a moving device (not illustrated) for moving the sample container holder H in forward and back directions within a range indicated by the dashed line.

FIG. 3B shows the structure of the sample container holder H. The sample container holder H has a container receiver H1 configured as a cylindrical hole, and a notch H2 which opens the container receiver H1 to the outside on the X-axis positive side of the container receiver H1. The notch H2 is formed to allow the barcode label BL1 of the sample container T to be read by the barcode unit B2, which will be described later. A spherically shaped depression H3 is also provided at the bottom of the container receiver H1.

The diameter of the container receiver H1 is larger than the diameter of the sample container T. The sample container T is held in the holder H with a predetermined clearance by inserting the sample container T into the container receiver H1 from above. At this time the bottom of the sample container T rests on the spherical depression H3. Hence, the bottom of the sample container T regulates movement in the direction parallel to the X-Y plane. Since the diameter of the container receiver H1 is greater than the diameter of the sample container T, the sample container T is movable in the direction parallel to the X-Y plane at the top end position of the container receiver H1. The sample container T is therefore supported in the sample container holder so that the top can be shaken.

FIG. 4 schematically shows the operation from the agitation of the sample container T until the color of the cap is detected. Note that FIGS. 4B and C show cross sections of the sample container holder H cut on a plane parallel to the X-Z plane connected at the center axis.

When the sample container T is removed from the sample rack L by the hand parts F15a and F15b, the hand parts F15a and F15b rotate 120 degrees in the counter clockwise direction parallel to the X-Z plane pivoting on a rotating shaft F11, as shown in FIG. 4A. The hand parts F15a and F15b then rotate in the clockwise direction pivoting on the rotation shaft F11. This operation is repeated numerous times. In this way the sample container T is moved so that the bottom of the sample container T is higher than the head, and the whole blood sample in the sample container T is thereby agitated. Note that when the sample container T is oscillated to the point of being turned over in this manner, the whole blood remains on the inner side of the cap due to the shape of the cap and the viscosity of the whole blood when the sample container T is returned to an upright state.

When the agitation operation ends, the hand parts F15a and F15b move downward (Z-axis negative direction), and the sample container T is accommodated in the container receiver H1 of the sample container holder H, as shown in FIG. 4B and FIG. 4C. In this state, the grip of the hand parts F15a and F15b is temporarily released, the bottom of the sample container T is set on the spherical depression H3, and thereafter the head of the sample container T is again gripped by the hand parts F15a and F15b. In this state, the white light from the white light source of the color sensor unit CS is irradiated on the cap of the sample container T, and the color of the cap is detected by the color sensor. Detection errors caused when the color detection is performed while the sample container T is inclined can be avoided since the white light source emits the white light while the head of the sample container T is gripped by the hand parts F15a and F15b.

When the cap color detection operation ends, the grip of the hand parts F15a and F15b is released from the sample container T, and the hand parts F15a and F15b are moved upward (Z-axis positive direction). Hence, it becomes possible to move the sample container holder H backward.

Returning to FIG. 3A, the barcode unit B2, which includes the barcode reader B2a for reading the barcode label BL1 of the sample container T, is disposed at the reading position P3 on the transport path of the sample container transporter 31 in the measurement unit 3. A piercer 32 for aspirating the whole blood sample from the sample container T is also disposed at the aspiration position P4 on the transport path of the rack transporter 23 in the measurement unit 3.

The sample container T supported in the sample container holder H at the take-up position P2 is then moved to the reading position P3, and the barcode label BL1 is read. Thereafter, the sample container T is moved to the aspirating position P4. At the aspirating position P4, the piercer 32 penetrates the cap installed on the sample container T, and aspirates the whole blood sample from the sample container T. The aspirated whole blood sample is measured in the measuring section (not illustrated) of the measurement unit 3.

Note that while reading the barcode label BL1 at the reading position P3, a suitable process is performed to remove the whole blood sample adhered to the inner side of the cap in the barcode unit B2.

When the aspiration of the whole blood sample ends at the aspiration position P4, the sample container holder H is moved forward and the sample container T is again disposed at the take-up position P2. At the take-up position P2, the sample container T is removed in an upward direction by the hand parts F15a and F15b. In this state, the sample container holder H is moved backward, and thereafter the hand parts F15a and F15b are moved downward (Z-axis negative direction). The sample container T is thus returned to the original holder of the sample rack L positioned on the rack transporter 23.

When the measurement is completed for the whole blood samples in the sample containers T held in the sample rack L, the sample rack L is moved to the left end position of the rack transporter 23. Thereafter, the sample rack L is pushed to a position to the back of the left table 22 by a rack pusher 23a. The sample rack L, which is placed at a position at the back of the left table 22, is then moved to the front of the left table 22 by the rack mover 22a.

FIG. 5 shows the structure of the gripping unit F for removing the sample container T from the sample rack L. FIG. 5A is a plan view of the gripping unit F viewed from the top side (Z-axis negative direction); B is a side view of the gripping unit F viewed from the right side (X-axis positive direction).

Referring to FIGS. 5A and B, the gripping unit F has a supporting body F10 and a base F20, Installed on the supporting body F10 are a rotating shaft F11, air cylinder F12, support plates F13 and F14, hand parts F15a and F15b, shaft F16, and spring F17.

The supporting body F10 is supported on the base F20 so as to be rotatable around the rotating shaft F11. The rotating shaft F11 is attached to the flanges F10a and F10b of the supporting body F10. One end of the rotating shaft F11 is supported so as to be rotatable on the flange F20b of the base F20, and the other end is attached to the drive-shaft of a step motor F18 mounted on the base F20. When the step motor F18 is actuated, the supporting body F10 is rotated around the rotating shaft F11, and the air cylinder F12, support plates F13 and F14, hand parts F15a and F15b, shaft F16, and spring F17 also rotated integratedly therewith.

The hand parts F15a and F15b pass through the rotating shaft F11, as shown in FIG. 3A. The hand part F15a is movable along the rotating shaft F11. The support plates F14 and F13 are respectively attached to the hand parts F15a and F15b. The support plate F13 is attached to the shaft F16 mounted on the supporting body F10. The support plate F14 is connected to a shaft F12a that extends from the air cylinder F12. The hole of the support plate F14 passes through the shaft F16. The air cylinder F12 moves the shaft F12a in the Y-axis direction. When the air cylinder F12 is actuated, the drive force is transmitted to the hand part F15a through the shaft F12a and the support plate F14, so that the hand part F15a moves along the rotating shaft F11.

Both ends of the spring F17 are attached to the support plates F13 and F14. The spring F17 pushes the support plate F14 in the Y-axis negative direction via an expansion action. The step motor F18 is mounted on the base F20. As described above, the end of the rotating shaft F11 in the Y-axis direction is attached to the drive-shaft of the step motor F18.

Pulleys F21a and F21b are provided on the inner wall 33a of the measurement unit 3 so as to be rotatable on the Y-axis, as a structure for moving the base F20 in the Z-axis direction. A step motor F23 and guide 33b are also provided on the inner wall 33a. The pulley F21a is provided on the shaft of the step motor F23 so as to be rotatable on the Y-axis. A belt F22 is looped around the pulleys F21a and F21b, and the base F20 is attached to the belt F22. A receiver F24 is provided on the base F20. The base F20 is thus movable in the Z-axis direction along the guide 33b through the receiver F24.

When the shaft F12a is moved in the Y-axis positive direction against the spring F17 by the air cylinder F12 from the state shown in FIGS. 5A and B, the hand part F15a is moved in the Y-axis positive direction along the rotating shaft F11. Hence, the head (cap) of the sample container T positioned between the hand parts F15a and F15b is gripped by the hand parts F15a and F15b. However, when the air cylinder 12 moves the shaft 12a in the Y-axis negative direction, the hand part F15a is set at the position shown in FIG. 5A and the grip on the cap is released from the state of the cap being gripped by the hand parts F15a and F15b.

When the step motor F18 is actuated, the rotating shaft F11 rotates on the Y-axis and the hand parts F15a and F15b also rotate on the Y-axis together with the supporting body F10. When the step motor F23 is actuated, the belt F22 moves and the base F20 moves in the Z-axis direction.

As described in reference to FIG. 4, the gripping unit F removes the sample container T from the sample rack L and tumble stirs the sample container T. After the sample container T has been tumble stirred by the gripping unit F, the sample container T is set in the sample container holder H; after the measurements have been completed, the sample container T is removed from the sample container holder H and returned to the original holding position on the sample rack L.

FIG. 6 shows the detailed structure of the barcode unit B2. Note that the barcode unit B1 differs from the barcode unit B2 only in the aspect that the notch B21a is formed in the roller B21; hence, the description is abbreviated.

FIG. 6A is a plan view showing the vicinity of the rollers B11 and B21 viewed from above; B is a side view of the barcode unit B2 viewed from the back (Y-axis negative direction).

Referring to FIGS. 6A and B, the barcode unit B2 has a supporting body B10, supporting body B20, and base B30. Two rollers B11, shaft B15, and light shield B18 are mounted on the supporting body B10. The supporting body B10 is supported so as to be movable in the X-axis direction by a guide (not illustrated) extending from the base B30 in the X-axis direction. The base B30 is attached inside the measurement unit 3. A sensor base B32 is provided on the base B30 to support the pulleys B13a and B13b, step motor B14, the previously mentioned barcode reader B2a, and transmission type sensor B31, which includes a light emitter and light receiver. The sensor base B32 is installed so as to extend in the Y-axis positive direction from the side surface that is parallel to the X-Z plane of the base B30.

The two rollers B11 are supported so as to be rotatable on the Z-axis via the supporting body B10. A belt B12 is looped around the pulleys B13a and B13b. The pulley B13a is installed on the shaft of the drive motor B14 so as to be rotatable on the Z-axis, and the pulley B13b is installed on the base B30 so as to be rotatable on the Z-axis. The belt B12 moves around the pulleys B13a and B13b by the drive of the step motor B14.

A support part B16 and spring B17 pass through the shaft B15. The support part B16 is movable a predetermined width in the Y-axis direction along the shaft B15. A collar B16a is formed on the support part B16, and the collar B16a is attached to the belt B12. The spring B17 pushes the support part B16 in the X-axis positive direction via an extension action.

When the belt B12 moves around the pulleys B13a and B13b, the support part B16 including the collar B16a also moves in the X-axis direction. When the collar B16a is moved in the X-axis negative direction, the support part B16 presses the spring B17 in the X-axis negative direction and the supporting body B10 moves in the X-axis negative direction. However, when the collar B16a is moved in the X-axis positive direction, the supporting part B16 presses the side surface of the supporting body B10 parallel to the Y-Z plane in the X-axis positive direction, and hence the supporting body B10 moves in the X-axis positive direction.

Light blockers B18a and B18b are formed on the light shield plate B18 on a plane perpendicular to the Y-axis. The light blockers B18a and B18b are configured to be positioned between the light emitter and the light receiver of the sensor B31 when the supporting body B10 is moved in the X-axis direction. When the barcode reader B2a is positioned on the front surface (X-axis positive direction) of the target sample container T, the supporting body B10 is moved in the X-axis negative direction from the state wherein the light blocker B18a is positioned between the light emitter and the light receiver of the sensor B31, as shown in FIGS. 6A and B.

When the supporting body B10 is moved in the X-axis negative direction in this manner, the two rollers B11 contact the side surface of the sample container T. At this time, in conjunction with the movement of the belt B12, the support part B16 moves in the X-axis negative direction as the spring B17 contracts, and the supporting body 10 does not move in the X-axis negative direction. Hence, it is understood that when the support part B16 has moved a predetermined width, the sample container T is maintained in the sample container holder H insofar as the light shield B18b is not positioned between light emitter and the light receiver of the sensor B31.

However, when the sample container T is not maintained in the sample container holder H and the supporting body B10 moves a predetermined width in the X-axis negative direction, The light shield B18b is positioned between the light emitter and the light receiver of the sensor B31. It is thus understood that the sample container T is not maintained in the sample container holder H.

When the mechanism for driving the supporting body B10 is configured in this way and the supporting body B10 is moved in the X-axis direction, the presence or absence of a sample container T can be detected in the sample container holder H positioned on the front side of the barcode reader B2a via the width of movement obtained from the step motor B14 and the detection signal from the sensor B31. When a sample container T is detected, the sample ID of the sample container T is read by the barcode reader B2a.

Referring to FIG. 6B, the roller B21, shaft B22, and pulley B24b are mounted on the supporting body B20. The supporting body B20 is screwed onto the base B30.

A notch B21a is formed on part of the outer circumferential surface of the roller B21. The edge of the notch B21a which reaches the sample container T first in the rotation of the roller B21 is recessed toward the center direction of the roller B21.

That is, this edge of the notch B21a forms a step-wise depression toward the center of the roller B21. The edge on the opposite side of the notch B21a is a curved surface smoothly connecting to the circular circumferential surface of the roller B21.

A through hole is formed in the Z-axis direction through the roller B21. The shaft B22 passes through this hole and supports the roller B21. Both ends of the shaft B22 are supported by the supporting body B20 so as to be rotatable in the Z-axis. The belt B23 is looped around the pulleys B24a and B24b. The pulley B24a is installed on the shaft of the drive motor B25 so as to be rotatable on the Z-axis, and the pulley B24b is installed on the base B30 and support shaft B22 so as to be rotatable on the Z-axis. The step motor B25 is mounted on the base F30.

When the mechanism for driving the roller B21 is configured in this manner, the belt B23 moves around the pulleys B24a and B24b through the drive of the step motor B25. Hence, the shaft B22 and the roller B21 are rotated on the Z-axis.

During the barcode reading operation, after the sample container holder H is positioned at the reading position P3 on the front side of the barcode unit B, the step motor B14 is actuated to move the supporting body B10 in the X-axis negative direction. At this time, when the sample container T is supported in the sample container holder H, the two rollers B11 contact the side surface of the sample container T so that the sample container T is disposed medially to the two rollers B11 and the roller B21. When the step motor B14 is actuated, the two rollers B11 are pushed from this state against the side surface of the sample container T by the force exerted by the spring B17. Thereafter, the step motor B14 is stopped, and the step motor B25 is then actuated. The roller B21 is thus rotated so that the sample container T is rotated while disposed medially to the two rollers B11 and the roller B21. In this state, the barcode label BL1 adhered to the sample container T is read by the barcode reader B2a.

FIG. 7 schematically shows the operation of the barcode unit B2 when the roller B21 has rotated. FIG. 7A through C respectively show the state of the sample container T and the rollers B11 when the roller B21 is at each rotation position; FIGS. 7D and F respectively show the sample container T when the roller B21 is at each of the rotation positions in FIG. 7A through C. Note that FIGS. 7D and F show cross sections of the sample container holder H cut on a plane parallel to the X-Z plane on the center axis.

When the roller B21 is at the rotation position shown in FIG. 7A, the sample container T is in the upright state indicated in FIG. 7D. In this case, the sample container T makes contact on the surface of the roller B21 outside the notch B21a, and the two rollers B11 press the side surface of the sample container T on the X-axis positive side. In this state, the roller B21 is driven in rotation in the clockwise direction. The sample container T is therefore rotated in the counterclockwise direction along its lengthwise axis in conjunction with the rotation of the roller B21.

When the rotation of the roller B21 continues from the state shown in FIG. 7A and the notch B21a of the roller B21 reaches the position of the sample container T, the head of the sample container T is pressed by the rollers B11 so as to be displaced in the X-axis negative direction. In this case, since the edge of the notch B21a on the right side in the circumferential direction is depressed toward the center of the roller B21, the head of the sample container T is moved quickly in the X-axis negative direction by the force exerted by the rollers B11, that is, the force exerted by the spring B17 as shown in FIGS. 6A and B. Since the sample container T is held in a state in which the head can be oscillated by the sample container holder H, the sample container T is moved so as to be inclined toward the right from the upright state as shown in FIG. 7E and described above. The part of the sample container T circumscribed by the dashed line in FIG. 7E strikes the top edge of the sample container holder H, thus jarring the sample container T via this movement.

When the whole blood sample adheres to the inner side of the cap CP due to the agitation operation shown in FIG. 4A, a force is applied to separate the whole blood sample adhered to the inner side of the cap CP from the cap CP by regulating the abrupt movement of the sample container T at the position indicated by the dashed line in FIG. 7E. The whole blood sample is dislodged from the inner side of the cap CP and falls into the sample container T via the application of this force. Note that in the state shown in FIG. 7E, the rotation of the sample container T is interrupted because the roller B21 is not in contact with the outer circumferential surface of the sample container T.

Note that when the whole blood sample is adhered to the inner side of the cap CP, a force is applied to separate the whole blood sample adhered to the inner side of the cap CP from the cap CP also in the stage shown in FIG. 7B. That is, in the stage shown in FIG. 7B, the sample container T is quickly displaced when pressed by the rollers B11, and this displacement causes a force in the opposite direction of the displacement to be applied to the whole blood sample adhered to the inner side of the cap CP. Hence, at this time also the whole blood sample adhered to the inner side of the cap CP can be expected to fall into the sample container T.

Thereafter, the sample container T returns to the upright position when the rotation of the roller B21 continues and the notch B21a of the roller B21 passes the position of the sample container T as shown in FIG. 7C. Then the sample container T again starts to rotate in the counterclockwise direction in conjunction with the rotation of the roller B21. Thus, a centrifugal force via the rotation and an inertial force via stopping the rotation are exerted on the whole blood sample adhered to the inner side of the cap CP through the repetition of the starting and stopping of the rotation of the sample container T.

Note that, when reading the barcode label BL1, the roller B21 rotates at low speed appropriate for reading the barcode label BL1, and rotates at high speed to remove the whole blood sample from the inner side of the cap CP during the operation to remove the whole blood sample from the cap CP. The barcode reader B2a reads the barcode label BL1 adhered to the sample container T through the notch H2 of the sample container holder H while the roller B21 rotates at low speed. In the present embodiment, the length of the roller B21 in the circumferential direction of the outer circumferential surface on which the notch B21a is not formed is slightly more than double the length in the circumferential direction of the outer circumferential surface of the sample container T. Therefore, when the roller B21 rotates, the sample container T rotates at least twice while in an upright state. The barcode label BL1 can thus be accurately read by the barcode reader B2a while the sample container T is rotated twice in an upright state.

Figure 8D:
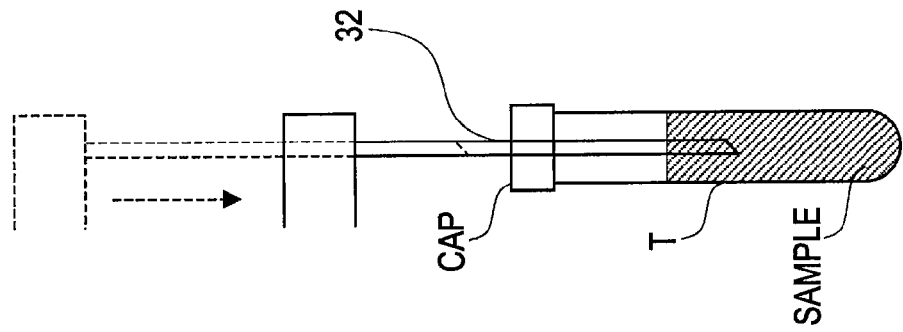
FIGS. 8A-8D show the structure of the piercer of the embodiment.
Figure 8C:
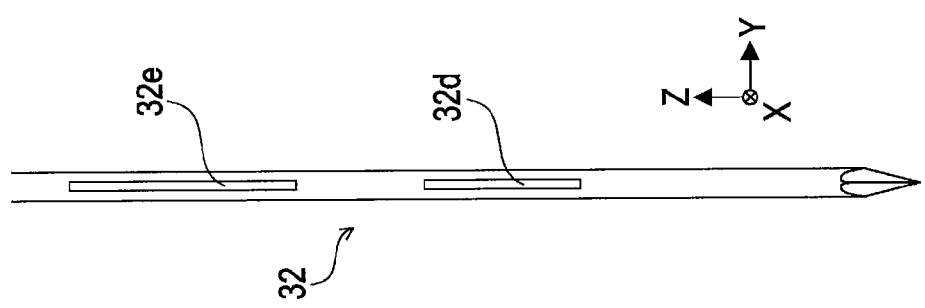
Figure 8A:
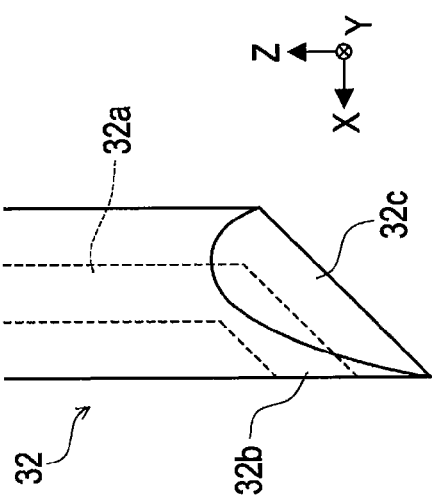
Figure 8B:
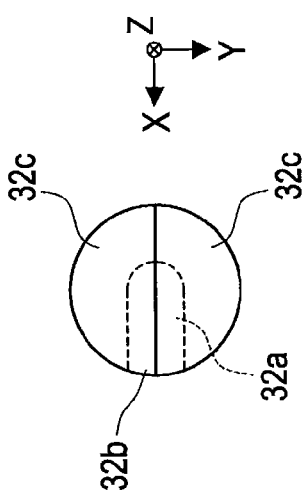

FIGS. 8A and B are enlargements showing the bottom end of the piercer 32 viewed from the side surface, and from the bottom side, respectively. FIG. 8C shows the structure of the body of the piercer 32. FIG. 8D shows the aspiration operation of the piercer 32.

A vertical aspirating channel 32a is formed inside the piercer 32. The aspirating channel 32a is curved leftward in the vicinity of the bottom end of the piercer 32, and is open to the outside through an orifice 32b. Two notches 32c, which are symmetrical relative to the Y-Z plane, are formed at the bottom end of the piercer 32. The bottom end of the piercer 32 forms a pointed shape by the two notches 32c. Due to this configuration of the piercer 32, when the piercer 32 descends from above the sample container T, the bottom end of the piercer 32 penetrates the cap and advances into the sample container T.

As shown in FIG. 8C, Channels 32d and 32e extending in the lengthwise direction are formed on the side surface of the piercer 32 on the X-axis negative side. The shape of the channels 32d and 32e when the piercer 32 is cut on the surface parallel to the X-Y axis is a V-shape with the depression toward the center of the piercer 32. As shown in FIG. 8D, the channels 32d and 32e perform the role of reducing the pressure within the sample container T to atmospheric pressure by communicating the inside of the sample container T with the outside.

The pressure within the sample container T is higher than atmospheric pressure. This pressure differential is the result of compression of the air when the cap is pressed onto the head of the sample container T after the whole blood sample is received into the sample container T. The aspirated amount of whole blood sample will not be stable when a whole blood sample is aspirated while there is a high pressure within the sample container T. The channels 32d and 32e reduce the high pressure within the sample container T to atmospheric pressure to maintain a constant uptake amount when aspirating samples. However, since the air within the sample container T may flow out through the channels 32d and 32e when the channels 32d and 32e pass through the cap, it is possible that whole blood sample remaining on the inner side of the cap may leak out through the channels 32d and 32e.

In the present embodiment, a suitable process is performed to remove the whole blood sample remaining on the inner side of the cap before the piercer 32 penetrates the cap, hence, leakage of the whole blood sample to the outside through the channels 32d and 32e is prevented when the cap is penetrated by the piercer 32.

Figure 9:
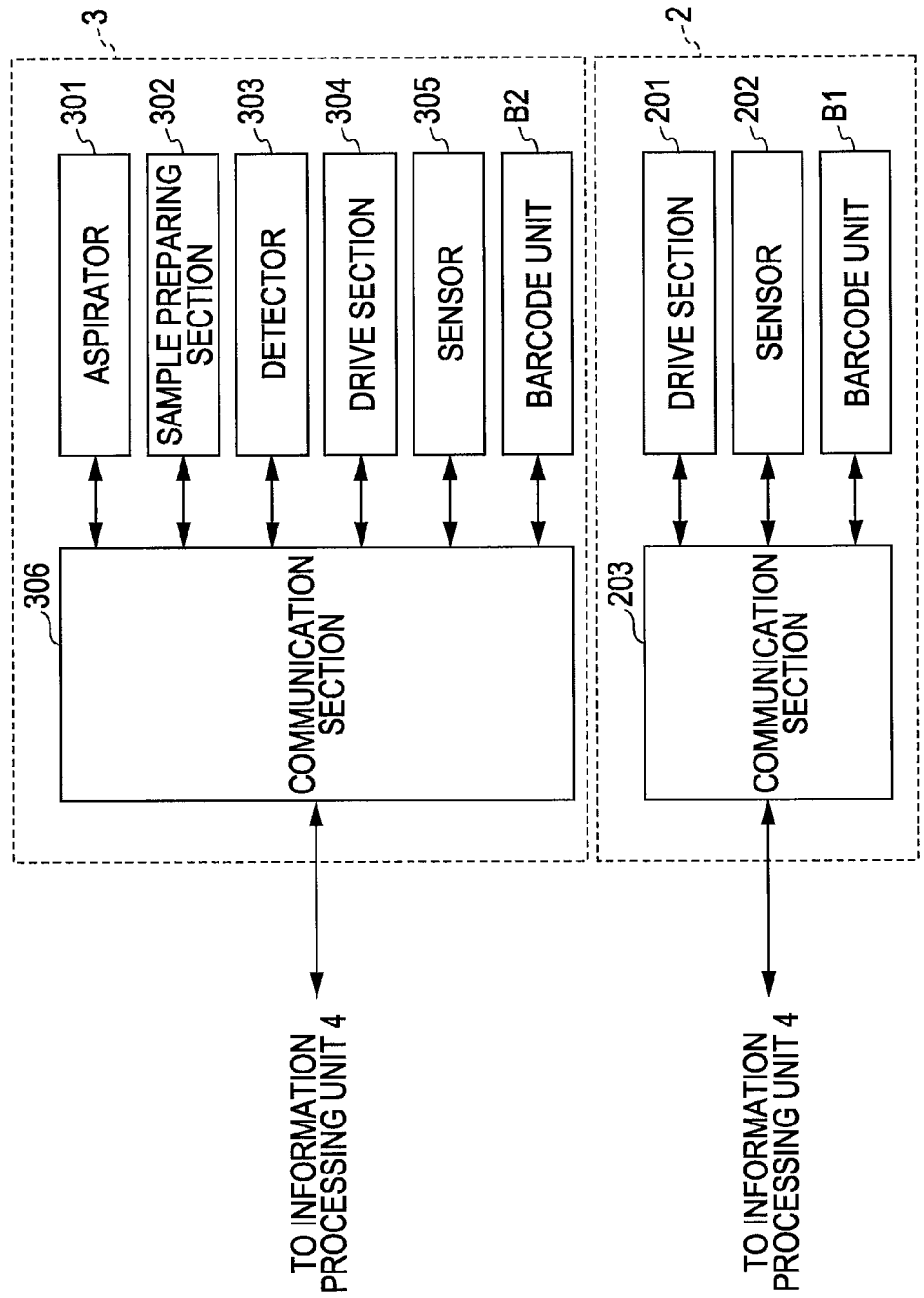
FIG. 9 shows the structures of the transporting

FIG. 9 shows the structures of the transporting unit 2 and the measurement unit 3.

The transporting unit 2 has a drive section 201, sensor section 202, barcode unit B1, and communication section 203.

The drive section 201 includes a device for moving the sample rack L within the transporting unit 2, and the sensor section 202 includes sensors for detecting the sample rack L at various positions within the transporting unit 2. The barcode unit B1 includes a barcode reader B1a.

The communication section 203 is connected to the information processing unit 4 and is capable of communication therewith. Each section of the transporting unit 2 is controlled by the information processing unit 4 through the communication section 203. Signals output from the various section in the transporting unit 2 are also transmitted to the information processing unit 4 through the communication section 203.

The measurement unit 3 has an aspirating section 301, sample preparing section 302, detecting section 303, drive section 304, sensor section 305, barcode unit B2, and communication section 306.

The aspirating section 301 includes a device for aspirating the whole blood sample in the sample container T through the piercer 32. The sample preparing section 302 includes reaction chambers, and within the reaction chambers a whole blood sample is mixed with diluting liquid and hemolytic agent as required to produce a sample for use in measurements. The detecting section 303 includes detectors of the electrical resistance type and detectors of the optical type, for detecting and counting the blood cells contained in the sample prepared by the sample preparing section 302.

The drive section 304 includes a device for driving the hand parts F15a and F15b, device for driving the sample container transporter 31, device for moving the piercer 32 within the measurement unit 3, device for moving the sample container within the measurement unit 3, and drive sources such as step motors for imparting a drive force to the various devices. The sensor section 305 includes sensors for detecting the sample container T at each position within the measurement unit 3. The barcode unit B2 includes a barcode reader B2a as described above.

The communication section 306 is connected to the information processing unit 4 and is capable of communication therewith. Each section of the measurement unit 3 is controlled by the information processing unit 4 through the communication section 306. Signals output from the various section in the measurement unit 3 are also transmitted to the information processing unit 4 through the communication section 306.

Figure 10:
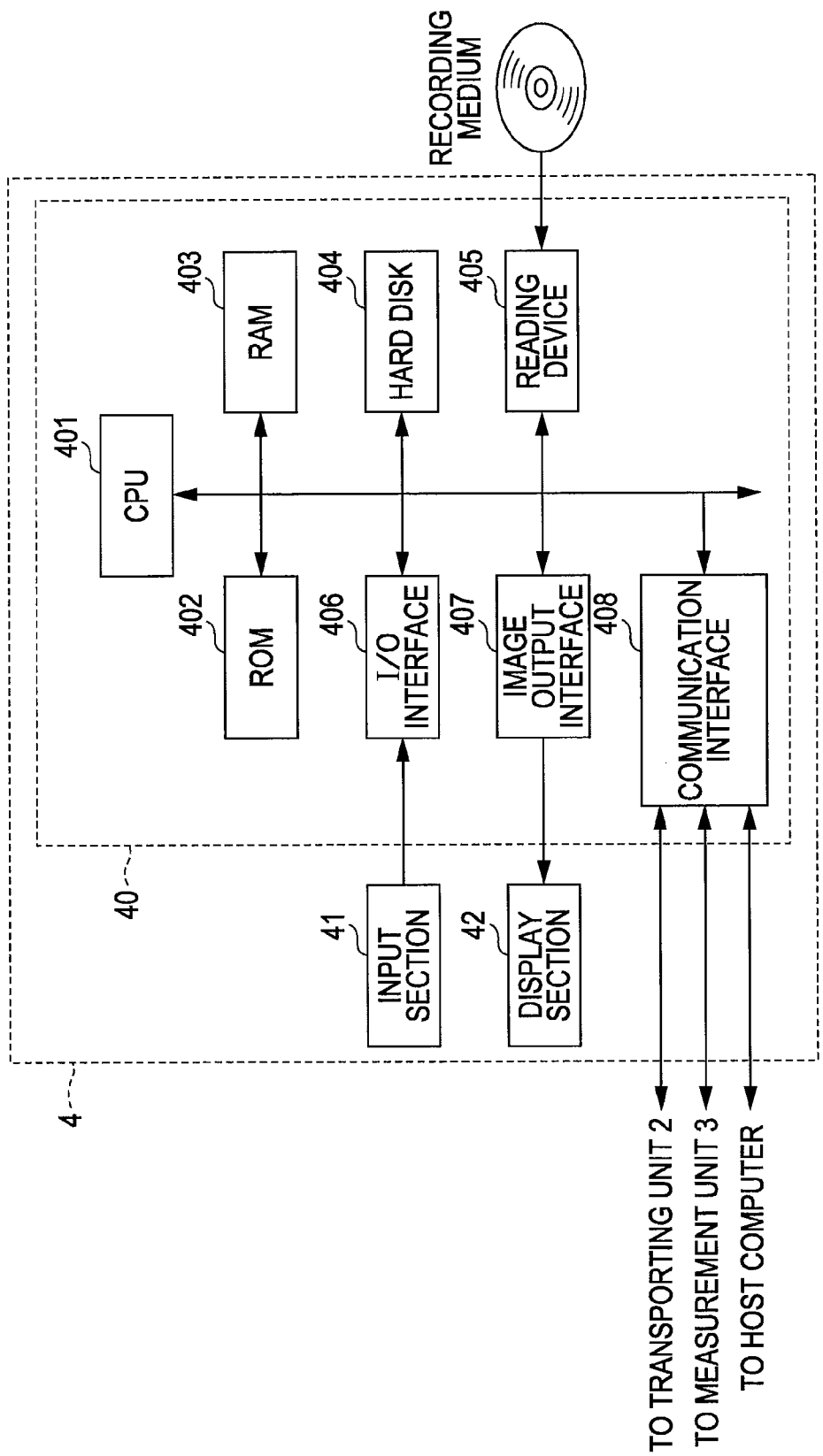
FIG. 10 shows the structure of the information processing unit of the embodiment.

FIG. 10 shows the structure of the information processing unit 4.

The information processing unit 4 is configured by a personal computer having a main body 40, input section 41, and display section 42. The main body 40 has a CPU 401 ROM 402, RAM 403, hard disk 404, reading device 405, I/O interface 406, image output interface 407, and communication interface 408.

The CPU 401 is capable of executing a computer program stored in the ROM 402 and a computer program loaded in the RAM 403. The RAM 403 is used when reading the computer program stored in the ROM 402 and recorded on the hard disk 404. The RAM 403 is also used as the work area of the CPU 401 when the CPU 401 executes the computer programs.

The hard disk 404 stores an operating system and application programs, as well as the data used when executing the operating system and application programs that are executed by the CPU 401. Specifically, the stored programs and data include programs and data used for measurements and analyses, and programs and data for controlling each section of the measurement unit 3 and the transporting unit 2 in addition to brightness threshold data used to identify the specific cap CP and brightness threshold data used to detect whether a cap is installed on the sample container T.

The reader 405 is a CD drive or DVD drive capable of reading computer programs and data recorded on a recording medium. The I/O interface 406 is connected to the input section 408 configured by a mouse and keyboard, and the user uses the input section 408 to input instructions and data to the information processing unit 4. The image output interface 407 is connected to the display section 42 configured by a CRT or liquid crystal panel or the like, and the image output interface 407 outputs image signals corresponding to the image data to the display 42. The display section 42 displays images based on the input image signals. Data transmission and reception is possible with the transporting unit 2, measurement unit 3, and host computer via the communication interface 408.

FIG. 11 is a flow chart showing the processes performed by the information processing unit 4 when the sample container T has arrived at the take-up position P2.

When the sample container T reaches the take-up position P2 (S101: YES), the CPU 401 controls the holding unit F to extract the sample container T from the sample rack L and perform the agitation operation shown in FIG. 4A several times (for example, ten times) (S102). The CPU 401 then transports the sample container holder H to the take-up position P2 and controls the holding unit F to place the agitated sample container T in the sample container holder H (S103) as described in reference to FIGS. 4B and C. The CPU 401 then executes the cap detection operation to operate the color sensor unit CS and detect the type of cap installed on the sample container T (S104) as described with reference to FIG. 4 (c).

Thereafter, the CPU 401 actuates the sample container holder H to move the sample container T to the reading position P3 (S105). The CPU 401 controls the barcode unit B2, which reads the barcode label BL1 adhered to the sample container T as the sample container T is rotated at low speed (for example, 2.5 rotations per second) (S106). Thereafter, the CPU 401 determines whether the cap installed on the sample container T is a specific cap CP based on the detection result in step S104.

When the cap installed on the sample container T is not the specific cap CP (S107: NO), the CPU 401 moves the sample container T together with the sample container holder H to the aspirating position P4 (S109). However, when the cap installed on the sample container T is the specific cap CP (S107: YES), the CPU 401 controls the barcode unit B2 to and executes an operation to remove the whole blood sample adhered to the inner side of the specific cap CP by rotating the sample container T several times (for example, five times) at high speed (for example, five rotations per second) (S108). In this operation the head of the sample container T is displaced as described referring to FIG. 7, and the side surface of the sample container T strikes the top edge of the sample container holder H several times (for example, five times, thus jarring the sample container T. The whole blood sample adhered to the inner side of the specific cap CP thus falls into the sample container T. Thereafter, the CPU 401 moves the sample container T together with the sample container holder H to the aspirating position P4.

When the sample container T reaches the aspirating position P4, the CPU 401 executes the operation to lower the piercer 32 and aspirate the whole blood sample within the sample container T as shown in FIG. 8D (S110). At this time, the piercer 32 passes through the cap installed on the sample container T. The pressure within the sample container T is reduced to atmospheric pressure by the channels 32d and 32e formed on the side surface of the piercer 32.

When the aspiration operation ends, the CPU 401 moves the sample container T together with the sample container holder H to the take-up position P2, and controls the holding unit F to return the sample container T held in the sample container holder H back to the original holding position in the sample rack L (S111). The processing related to this sample container T therefore ends. Thereafter, the CPU 401 returns to step S101 and moves the next sample container T to the take-up position P2.

Figure 11A:
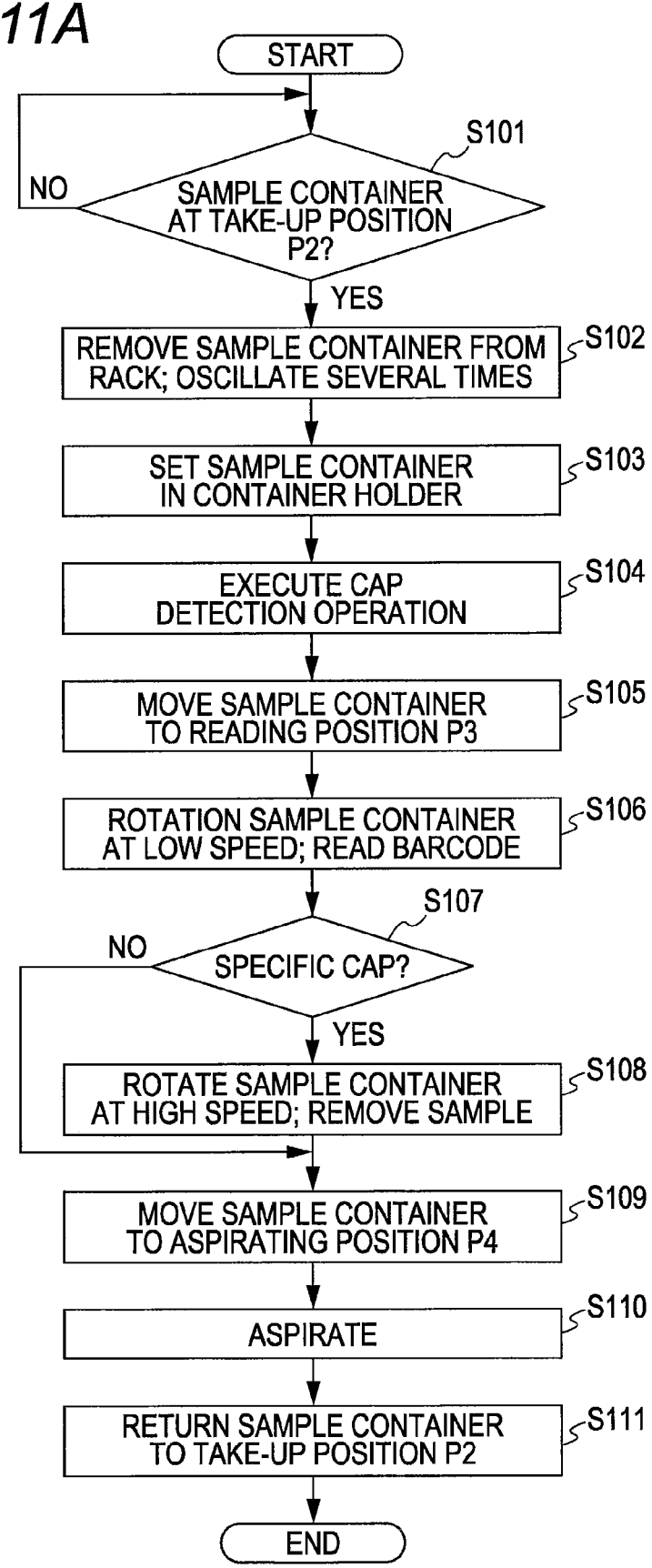
FIGS. 11A and 11B are flow charts showing the operation of the measurement unit of the embodiment.
Figure 11B:
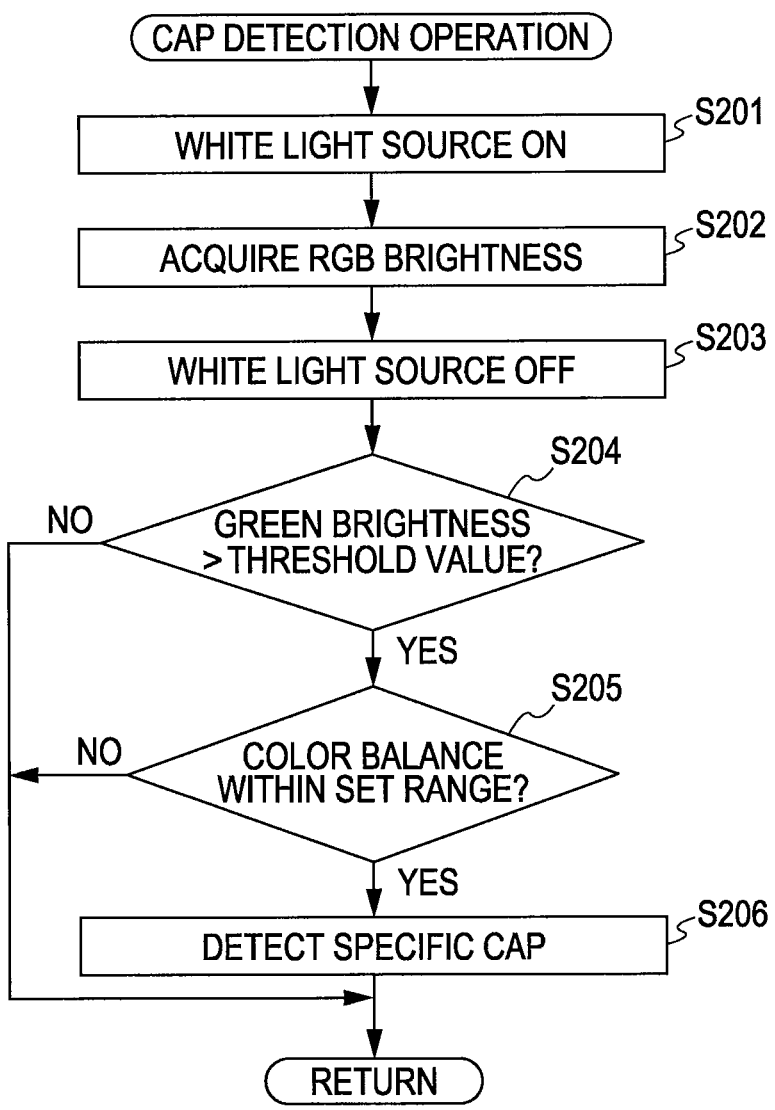

FIG. 11B is a flow chart showing the cap detection operation in step S104 of FIG. 11A.

During the cap detection operation, the CPU 401 turns on the white light source of the color sensor unit CS to irradiate white light on the cap installed on the sample container T (S201). Then the CPU 401 operates the color sensor to acquire the data relating to the brightness of red, blue, and green colors from the cap irradiated by the white light (202). When the brightness data are acquired, the CPU 401 turns of the white light source (S203).

After the brightness data are acquired, the CPU 401 determines whether the brightness of the acquired green color exceeds a threshold value which has been previously set to detect the presence of an installed cap. When the acquired green color brightness value does not exceed the threshold value (S204: NO), the CPU 401 determines that a cap is not installed on the sample container T, and the cap detection process ends. In this case, the specific cap has not been detected. However, when the acquired green color brightness does exceed the threshold value (S204: YES), the CPU 401 determines that a cap of some type is installed on the sample container T, and the process advances to step S205.

In step S205, the CPU 401 determines whether the brightness balance of the acquired red, green, blue colors (color balance) is within a preset range used to identify the color of the specific cap (milk white color) (S205). Specifically, when the acquired red, green and blue color brightness is represented by R, G, B, the relationship 1−a<R/G obtains; that is, when the relationship R/G<1+bis satisfied, the red, green, blue brightness balance (color balance) is determined to be within a range set to identify the color (milky white) of the specific cap. In this relationship, the values a and b are adjustment constants for detecting the specific cap even when the color of the specific cap is somewhat dull.

When the determination of step S205 is YES, the CPU 401 detects the cap installed on the sample container T as a specific cap (S206). However, when the determination of step S205 is NO, the CPU 401 detects the cap installed on the sample container T as a nonspecific cap, and the cap detection process ends. In this case, the specific cap has not been detected.

According to the present embodiment, the whole blood sample can be removed from the inner side of the specific cap CP before aspiration even when the whole blood sample is adhered to the inner side of the specific cap CP due to the whole blood sample agitation operation because a force is applied to the sample container T to remove the whole blood sample from the inner side of the specific cap CP before the whole blood sample is aspirated. This prevents leakage of the whole blood sample at the top of the specific cap CP from the piercing location even though the piercer 32 penetrates the specific cap CP during aspiration.

Note that the present embodiment is particularly suited to preventing ejection of the blood with the air within the sample container when the air is released from a sample container having a higher air pressure than atmospheric pressure as in the example of the sample container which is sealed by pressing on a cap after the whole blood sample is put in. The type of sample container applicable to the present invention is not limited inasmuch as the present invention is applicable to any vacuum blood collection tube.

Note that although the roller B21 is rotated several times (for example, five rotations) and the sample container T is displaced from an upright state several times (five times) in the present embodiment, the roller B21 also may be rotated a single rotation during the sample removal operation when whole blood sample can be removed from the inner side of the specific cap CP by a single displacement of the sample container T.

According to the present invention, a rapid inertial force, that is, a shock, is exerted on the whole blood sample adhered to the inner side of the specific cap CP by regulation of the displacement when the head of the sample container T is oscillated and displaced such that the side surface of the sample container T contacts the top edge of the sample container holder H to abruptly regulate the displacement of the sample container T. Hence, the whole blood sample adhered to the inner side of the cap can be smoothly removed.

According to the present embodiment, since the roller B21 of the barcode unit B2 is provided with a notch B21a to effect displacement the sample container T, a special mechanism is not required to displace the sample container T, hence, simplifying the structure needed for whole blood sample removal.

According to the present embodiment, the sample container T can be rapidly displaced toward the center of the roller B21 when the notch B21a reaches the sample container T because the rotational speed of the roller B21 during the sample removal operation is faster than the rotational speed of the roller B21 during the barcode reading operation. That is, After the front end of the notch B21a reaches the sample container T, the circumferential surface of the sample container T has sliding contact with the front end of the notch B21a so as to move toward the center of the roller B21. Therefore, when the rotational speed of the roller B21 accelerates, the circumferential surface of the sample container T has a shorter period of sliding contact with the front end of the notch B21a, with the result that the speed of the ample container T is increased toward the center of the roller B21. In addition, the sample removal operation can be completed in less time to rapidly shift to the sample aspiration operation by increasing the rotational speed of the roller B21 during the sample removal operation.

According to the present embodiment, since the sample removal operation (step S108 in FIG. 11A) is executed only when the specific cap CP has been detected, unnecessarily performing the sample removal operation is avoided when the sample container T is sealed with a cap to which the whole blood sample is unlikely to adhere, that is, when the sample container T does not require removal of the whole blood sample, hence, processing speed and efficiency are increased.

Note that in this case the specific cap is not detected when there is no cap installed and the top part of the sample container T is open, and as a result the sample removal operation is not executed for uncapped sample containers T. Therefore, whole blood sample spraying from the top of the sample container T when executing the sample removal operation on an uncapped sample container T can be avoided.

Although the present invention has been described above by way of an embodiment, the present invention is not limited to this embodiment.

Figure 12:
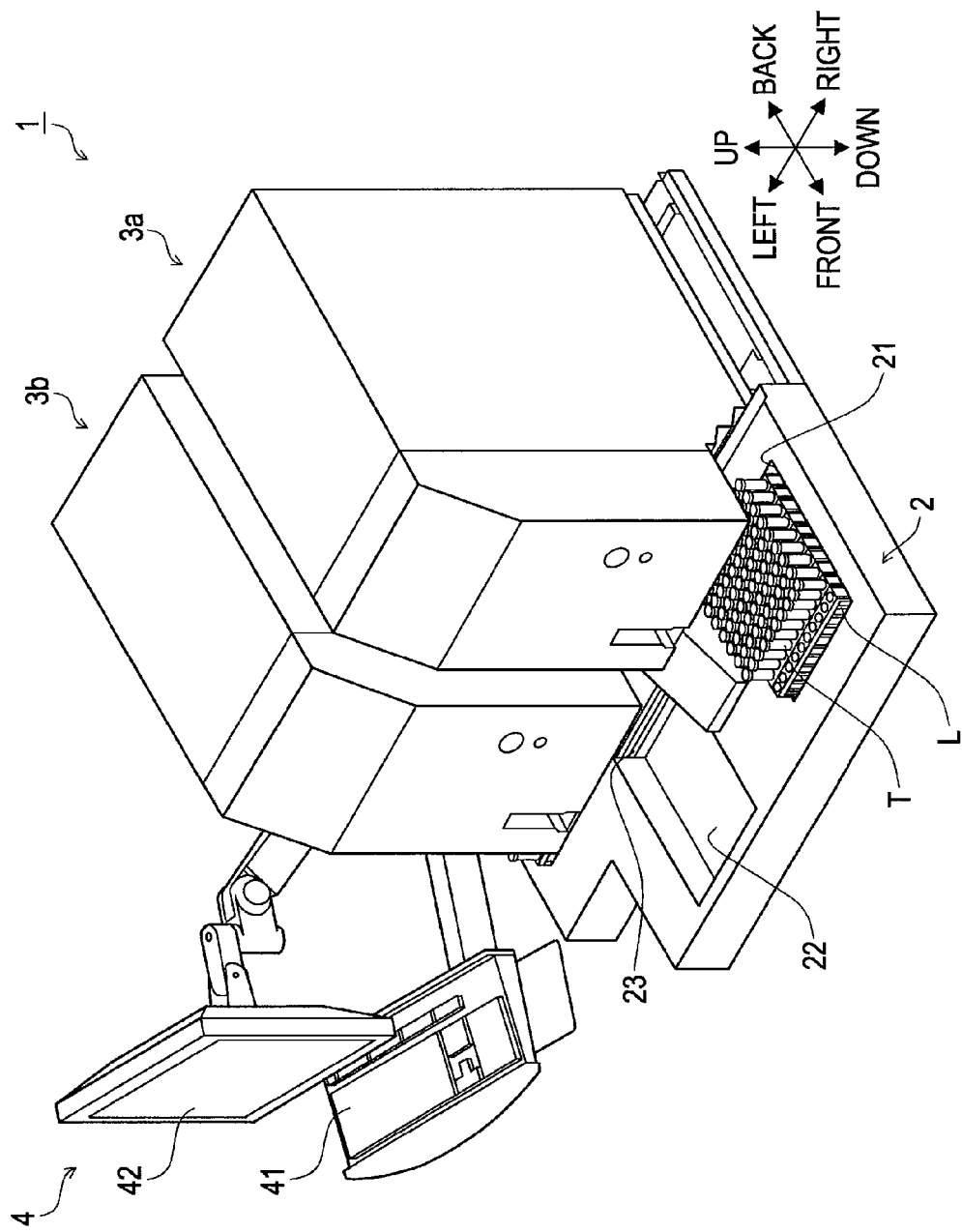
FIG. 12 is a perspective view showing an external view of a modification of the blood cell counting apparatus.

For example, although a blood cell counting apparatus 1 provided with a single measurement unit 3 is described in the example of the above embodiment, the number of measurement units 3 is not limited, inasmuch as the present invention is applicable to, for example, a blood cell counting apparatus 1 provided with two measurement units 3a and 3b, as shown in FIG. 12. In this case the measurement units 3a and 3b have the sample structure as the measurement unit 3 described in the above embodiment, and the sample agitation operation and sample removal operation are performed in each measurement unit 3a and 3b.

Although the sample removal operation (step S108 in FIG. 11A) is executed only when the specific cap CP is installed on the sample container T in the above embodiment, the sample removal operation also may be executed when a cap other than the specific cap CP is installed on the sample container T. It is undesirable to perform the sample removal operation on an uncapped sample container T since there is a possibility that whole blood sample will leak due to the shock imparted on the sample container T when the sample removal operation is executed for a sample container T that lacks a cap.

Figure 13A:
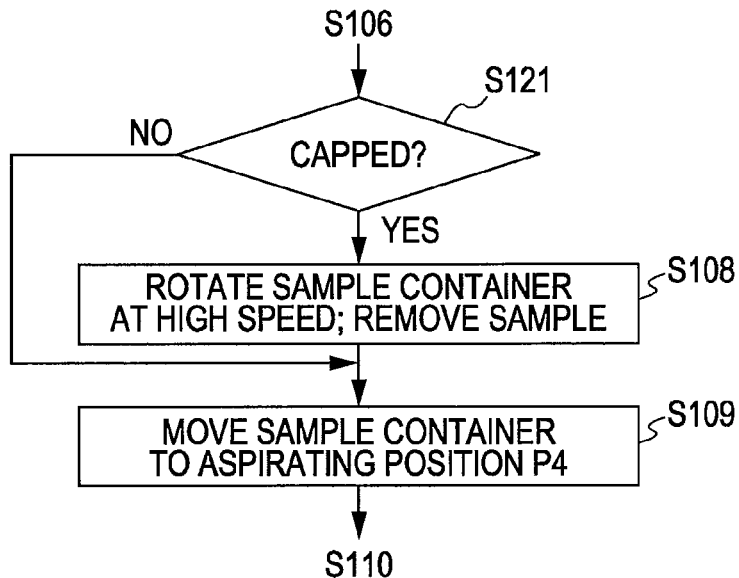
FIGS. 13A and 13B are flow charts showing the operation of the measurement unit of the modification.

FIG. 13A is a flow chart showing a modification when the sample removal operation is executed for all capped sample containers T. In this modification, the step S107 of FIG. 11A is substituted for step S121. The cap detection operation in step S104 of FIG. 11A is changed from FIG. 11B to FIG. 13B.

Figure 13B:
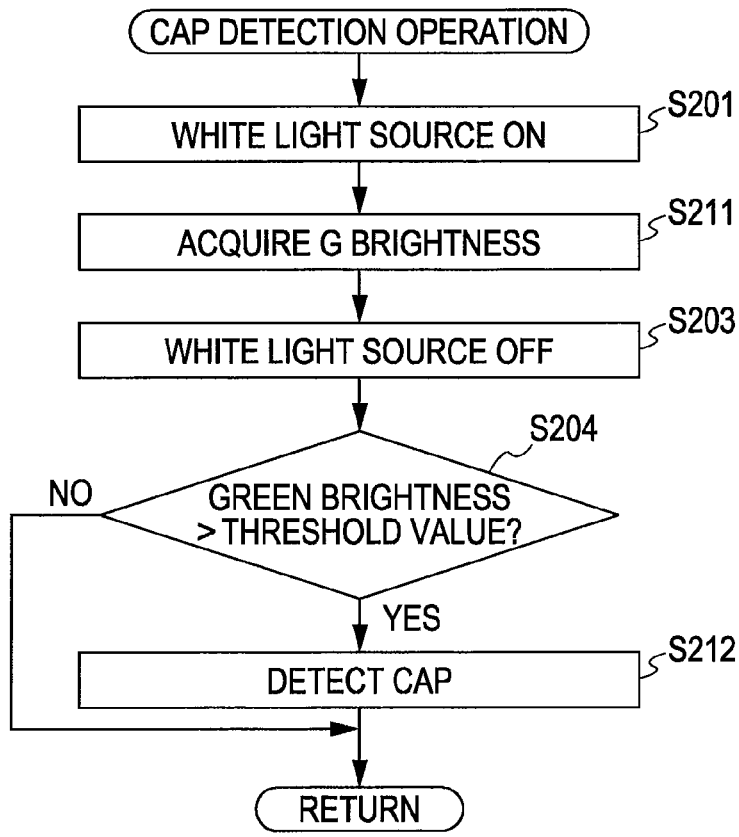

As shown in FIG. 13B, only green color brightness data are detected by the color sensor in this modification (S211). The presence of a cap is detected on the head of the sample container T (S212) when the detected green color brightness data exceeds the threshold value (S204: YES), and a cap is not detected on the head of the sample container T when the green color brightness data detected by the color sensor does not exceed the threshold value (S204: NO).

After reading the barcode label BL1 in step S106 of FIG. 13A, a determination is made whether the sample container T is capped based on the detection results of the cap detection operation in step S121 of FIG. 13B. The sample removal operation is executed in the step S108 when the sample container T is capped (S121: YES), and the sample container T is moved to the aspirating position P4 without executing the sample removal operation in step S108 when the sample container T is uncapped (S121: NO).

According to this modification, inefficient processing results from performing unnecessary sample removal operations for sample containers T that do not require the sample removal operation since the sample removal operation is executed for all capped sample containers T. Conversely, however, leakage of whole blood sample from the top surface of the cap is more thoroughly prevented during the aspiration operation by removing the whole blood sample from the cap even when the whole blood sample is very unlikely to adhere to the cap. Note that in this modification whole blood sample spraying from the uncapped sample container T is avoided because the sample removal operation is not executed on uncapped sample containers T.

Figure 14A:
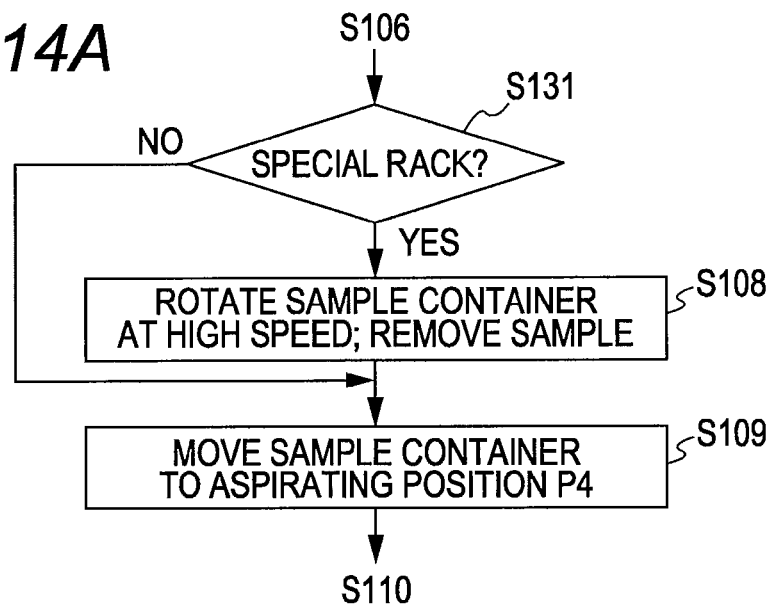
FIGS. 14A-14C are flow charts showing the operation of the measurement unit of the modification.

FIG. 14A is a flow chart showing the operation of a modification for determining whether to execute the sample removal operation for a sample container T according to the type of sample rack L. In this modification, step S104 of FIG. 11A is substituted by step S131, and step S104 of FIG. 11A is omitted. Also in this modification, the user installs the sample container T to be subjected to the sample removal operation in a special sample rack (special rack) SL, and places the sample rack SL on the right table 21. The special rack SL is identifiable by the rack ID bearing the barcode label BL1 shown in FIG. 2C.

In this modification, when the barcode label BL1 is read in step S106, whether the sample container T is installed in a special rack SL is determined in step S131. This determination is accomplished based on the rack ID read from the barcode label BL1 in the barcode unit B1. The sample removal operation of step S108 is performed when the sample container T is installed in a special rack SL (S131: YES), and the sample container T is moved to the aspiration position P4 without executing the sample removal operation in step S108 when the sample container T is not installed in a special rack SL (S131: NO) (S109).

According to this modification, when there is a possibility of whole blood sample adhering to the inner side of the cap, the user may set the sample container T in a special rack SL, and places the special rack SL on the right table 21. Thus, the sample removal operation is executed efficiently.

Figure 14B:
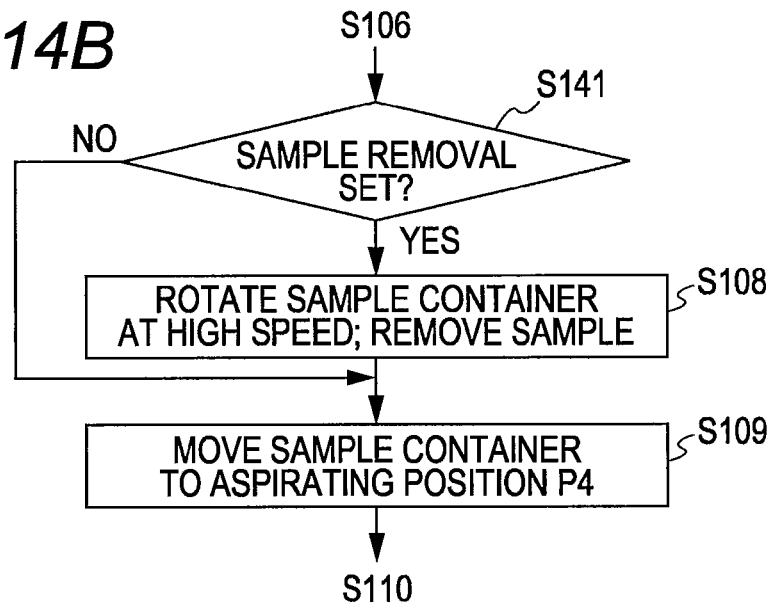
Figure 14C:
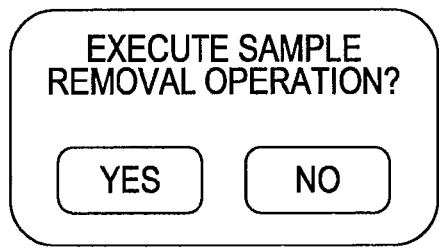

FIG. 14B is a flow chart showing a modified operation that is manually set by the user to determine whether to execute the sample removal operation on a sample container T. In this modification, step S107 of FIG. 11A is substituted by step S141, and step S104 of FIG. 11A is omitted.

In this modification, when recording an order for a sample container T, a dialog or the like is shown on the display section 42 of the information processing unit 4 as shown in FIG. 14B. Execution of the sample removal operation for the sample container T is set when the YES button is operated in the dialog box, and execution of the sample removal operation for the sample container T is not set when the NO button is operated.

Referring to FIG. 14b, when the barcode label BL1 is read in step S106, a determination is made whether the execution of the sample remove operation is set for the sample container T in step S141. The sample removal operation is executed in step S108 when the execution of the sample removal operation is set (S141: YES), and the sample container T is moved to the aspirating position P4 without executing the sample removal operation in step S108 when the execution of the sample removal operation is not set (S141: NO). This modification is suited for blood cell counting apparatuses that measure sample containers T placed one at a time in a measurement unit 3.

Note that the operation of FIG. 11A of the above embodiment and the modified operations of FIG. 13A and FIG. 14B are suited for a user to perform the agitation operation manually without performing an agitation operation in the measurement unit 3. For example, the operation according to these flow charts are suitable even when the measurement unit 3 has no agitation function.

In this case, for example, the sample container holder H is moved outside the measurement unit 3, and the manually agitated sample container T is placed directly in the sample container holder H. Thereafter, the measurement start button is operated to deliver the sample container holder H into the measurement unit 3 and the cap detection operation of step S104 is performed at a predetermined position on the transport path. Thereafter, the operations of steps S105 through S110 are executed. When the aspirating operation of step S110 is completed, the sample container holder H is moved outside the measurement unit 3 (S111), and the user removes the sample container T.

Since the whole blood sample adhered to the inner side of the cap during the manual agitation by the user can be removed before aspirating the whole blood sample, leakage of the whole blood sample adhered to the inner side of the cap to the outside of the cap can be prevented while aspirating the sample.

Although a single notch is formed on the roller B21 in the example of the above embodiment, the number of notches formed in the roller B21 is not limited to a single notch and may be a plurality of notches. A projection rather than a notch, or a notch and a projection also may be formed on the roller B21. The single roller having a shape to displace the sample container T may be a plurality of roller rather than a single roller.

Figure 15A:
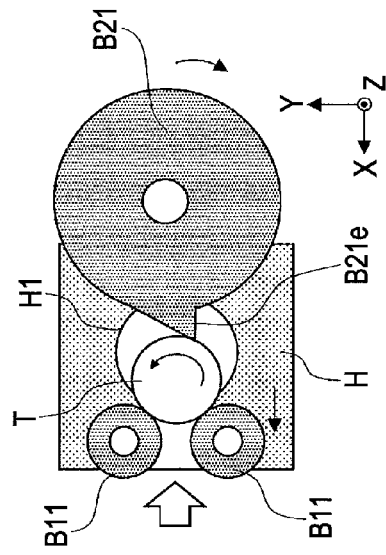
FIGS. 15A-15D show the structure of the roller of the modification.

FIG. 15A shows a modification when two notches are formed on the roller B21. In this modification, a notch B21b is formed in addition to the notch B21a of the above embodiment. The shape of the notches B21b is identical to the shape of the notch B21a. In this modification, the sample container T is displaced twice toward the center of the roller B21 during a single rotation of the roller B21, hence removing whole blood sample more efficiently than the above embodiment. In this case, the barcode label BL1 adhered to the sample container T is read between the contacts of the sample container T with the exterior surfaces B21c and B21d which do not have the notches B21a and B21b. The length in the circumferential direction of the exterior surfaces B21c and B21d is set to be greater than the length in the circumferential direction of the sample container T.

Figure 15B:
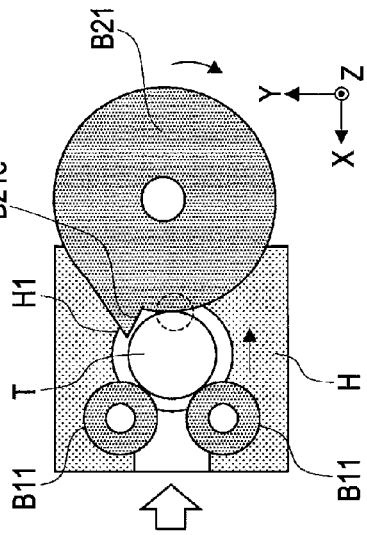
Figure 15C:
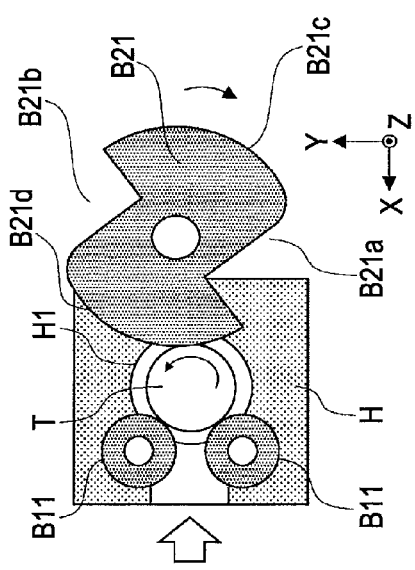
Figure 15D:
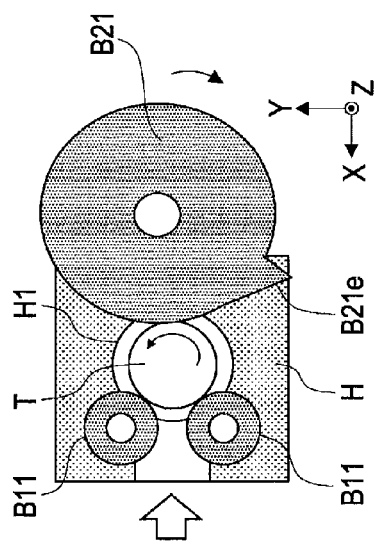

FIG. 15B through D shows modifications when a projection is formed on the roller B21. In this modification, the circumferential surface of the roller B21 is provided with a projection B21e which has an inclined surface that gradually increases the distance from the center of the roller B21. The terminal end of the inclined surface of the projection B21e returns, step-like, to a distance corresponding to the diameter of the circle of the roller B21.

When the rotation of the roller B21 advances from the state shown in FIG. 15B, the sample container T is pushed by the inclined surface of the projection B21e so that the sample container T and the rollers B11 are displaced in the X-axis positive direction against the force exerted by the spring B17 of FIG. 6. Thereafter, when the rollers B11 rotate, the terminal end of the projection B21e rides across the side surface of the sample container T from the state shown in FIG. 15C, and the sample container T is rapidly displaced toward the center of the roller B21 by the force exerted by the spring B17 as shown in FIG. 15D. When the sample container T is displaced, the head of the sample container T strikes the side surface of the roller B21 at the position indicated by the dashed circular line of FIG. 15D. The shock of this strike causes the whole blood sample adhered to the inner surface of the cap of the sample container T to fall into the sample container T.

Note that although a single projection is formed on the outer circumferential surface of the roller B21 in FIG. 15B through D, the number of projections is not limited inasmuch as a plurality of projections also may be formed on the circumferential surface of the roller B21. The shape of the projection is not limited to the triangular shape shown in FIG. 15B through D, and may also be trapezoidal or curved in shape. The terminal end of the projection must be formed so as to connect to the circumferential surface in a step-like fashion.

FIG. 16D shows a modification wherein a projection and a notch are provided on the circumferential surface of the roller B21. In this modification the terminal end of the projection B21g is connected to the initial end of the notch B21f. The notch B21f is identical to the notches B21a and B21b of FIG. 15A. The projection B21g is identical to the projection B21e of FIG. 15B. Note that the dashed line circle in FIG. 16A indicates the contour of the roller B21 when neither the notch B21f nor the projection B21g are provided.

According to this modification, the moving speed of the sample container T increases more than in the above embodiment when the sample container T reaches the notch B21f because the sample container T is displaced by the total distance of the height of the terminal end of the projection B21g and the initial end of the notch B21f. The speed increases when the sample container T contact the top edge of the sample container holder H, and a larger force is therefore exerted on the whole blood sample adhered to the inner side of the cap CP as shown in FIG. 7E. According to this modification, the whole blood sample removal action is thus enhanced.

Although structures are added to the roller B21 of the barcode unit B2 to increase the force (shock) on the sample container T in the above embodiment and modifications, a separate structure may be added to apply a force on the sample container T to remove the whole blood sample from the cap at a position other than the reading position P3 on the transport path of the sample container transporter 31. In this case, as stated above, a structure or separate form may be added to elastically grip the sample container T by a driven roller having a notch or projection formed on the circumferential surface, and two other rollers. For example, a structure may be provided to lightly strike the side surface of the sample container T to apply a force (shock) to the sample container T. Alternatively, a structure also may be provided to strike the cap of the sample container T from above apply a force (shock) to the sample container T.

Figure 16B:
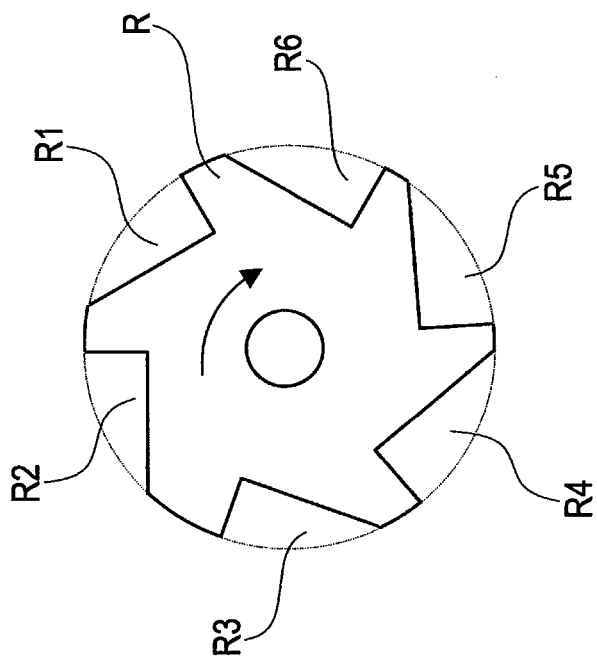
FIGS. 16A and 16B show the structure of the roller of the modification.
Figure 16A:
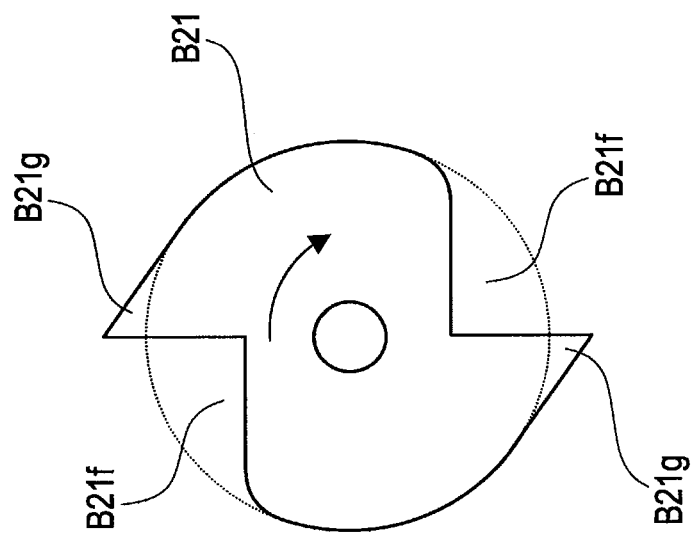

When a structure is provided to elastically grip the sample container T by a driven roller and another two rollers, a plurality of shallow notches R1 through R6 may be formed on the driven roller R as shown in FIG. 16B. Note that the dashed line circle in FIG. 16B indicates the contour of the roller R when the notches R1 through R6 are not provided.

In this case, when the notches R1 through R6 reach the position of the sample container T and the sample container T is displaced due to the shallow notches R1 through R6, the heat of the sample container T contact the side surface of the notches R1 through R6 and the side surface of the sample container T does not contact the top edge of the sample container holder H as shown in FIG. 7E, and a force to remove the whole blood sample from the cap is exerted on the whole blood sample adhered to the inner side of the cap. According to this modification, the efficiency of removing the whole blood is increased because the sample container is oscillated six times per each revolution of the roller R.

Furthermore, the shape of the roller itself may be elliptical rather than having a structure with concavity and projection on the circumferential surface of the roller. Since the sample container T oscillates in direction perpendicular to the longitudinal direction in conjunction with the rotation of the roller, the oscillation can be imparted to the whole blood sample adhered to the inner side of the cap. Therefore, the whole blood sample adhered to the inner side of the cap can be removed by adjusting the ratio of the long axis and short axis of the elliptical shape, or by adjusting the rotational speed of the roller.

A structure capable of gripping the bottom of the sample container T and oscillating the head of the sample container T may be used instead of the roller.

Although the specific cap CP is detected by color in the above embodiment, the specific cap CP also may be detected by shape. For example, in this case the cap installed on the sample container T can be detected as a specific cap CP by providing an imaging section within the measurement unit 3 to capture the image of the cap, and analyzing the capture image of the cap. Alternatively, the specific cap CP also may be detected by providing the specific cap CP with a mark so as to detect the mark.

The direction of the displacement of the sample container T during the sample removal operation is not limited to a direction transecting the longitudinal direction of the sample container inasmuch as direction of displacement also may be parallel to the longitudinal direction of the sample container. For example, a force to separate the whole blood sample from the cap may be imparted to the whole blood sample adhered to the inner side of the cap by lifting the sample container T from the sample container holder H, then lowering the sample container T into the sample container holder H so as to strike the bottom of the sample container T on the spherical depression H3 of the sample container holder H. Alternatively, the sample container T may be dropped into the sample container holder H rather than free fall to apply a force vertically downward. Specifically, a force may be imparted by striking the bottom of the sample container T by lifting the sample container T by the hand part, then dropping the sample container T into the sample container holder H by releasing the grip. Alternatively, inertia may also be imparted by elastically drawing the head of the sample container via an elastic body such as a spring, then rapidly moving the head by releasing the draw. Alternatively, an oscillation may be imparted to the sample container by an eccentric motor.

Although the embodiment is described in terms of tumble stirring the sample container T, that is, stirring the sample container so the bottom is higher than the head, various modification are possible insofar as the sample container is moved and the whole blood sample is stirred. For example, the sample container may be oscillated in a pendulum motion from an upright state to a horizontal state so as to adequately stir the whole blood sample by sufficiently increasing the speed of the pendulum motion. The present invention is not limited to the mode of stirring the sample container by gripping the hand part, inasmuch as the sample container also may be stirred by turning over the rack holding the sample container. The sample container also may be inverted.

The embodiment of the present invention is not limited to the above described embodiment and may be variously modified insofar as such modification are within the scope of the claims.

What is claimed is:

1. A blood cell counter comprising:
   a agitation device that mixes a whole blood sample in a sample container by moving the sample container;
   an aspirator that aspirates the whole blood sample by penetrating a lid of the sample container with an aspiration tube after mixing the whole blood sample;
   a detector that counts the blood cells in the whole blood sample aspirated by the aspirator; and
   a force applying member that applies a force to the sample container in an upright state after mixing so as to remove the whole blood sample from the lid of the sample container,
   wherein the force applying member comprises a roller that contacts an outer surface of the sample container and rotates the sample container around an axis parallel to the longitudinal direction of the sample container, and a force applicator that pushes the sample container to the roller while the sample container is rotated, and
   wherein a distance from an outer circumferential edge of the roller to a rotational center of the roller varies.

2. The blood cell counter of claim 1, wherein the force applying member moves the sample container by applying the force to the sample container so as to remove the whole blood sample from the lid of the sample container.

3. The blood cell counter of claim 2, wherein the force applying member moves the sample container in a direction transecting the longitudinal direction of the sample container by applying the force to the sample container.

4. The blood cell counter of claim 3 further comprising:
   a sample container supporter that supports at least a head of the sample container in the oscillating state, and the sample container in the upright state;
   wherein the force applying member applies the force to the sample container in a direction transecting the longitudinal direction of the sample container while the sample container is supported in the sample container supporter.

5. The blood cell counter of claim 4, wherein
   the force applying member rotates the roller at least one rotation while the roller is in contact with the outer surface of the sample container.

6. The blood cell counter of claim 5, wherein a barcode reader reads a barcode attached to the sample container while the sample container is rotated around the axis parallel to the longitudinal direction of the sample container; and wherein the roller rotates the sample container so that the barcode reader reads the barcode.

7. The blood cell counter of claim 6, wherein the barcode reader executes a first step that brings the outer surface of the roller into contact with the outer surface of the sample container and reads a barcode while rotating the sample container at a first speed, and a second step that rotates the sample container at a higher speed than the first speed and removes the whole blood sample adhered to the inner side of the lid.

8. The blood cell counter of claim 5, wherein the movement of the sample container is regulated by action of the sample container contacting the outer surface of the roller.

9. The blood cell counter of claim 4, wherein the movement of the sample container is regulated by action of the sample container contacting the sample container supporter.

10. The blood cell counter of claim 1, wherein the roller has different levels on the outer surface of the roller, the level changing the distance in steps from the rotational axis of the roller.

11. The blood cell counter of claim 1, wherein a transport section holds the sample container in an upright position after the whole blood has been mixed, and moves the sample container to an aspirating position of the sample aspirator; and wherein the force applying member applies the force on the sample container at a predetermined position on the transport path of the sample container in the transport section.

12. The blood cell counter of claim 1, further comprising a lid detector that detects a specific lid on the sample container; wherein the force applying member applies the force on a sample container having the specific lid detected by the lid detector, and refrains from applying the force on a sample container that does not have the specific lid detected by the lid detector.

13. The blood cell counter of claim 12, wherein the lid detector comprises a color sensor that detects a color of the lid affixed to the sample container, and detects whether the lid of the sample container is the specific lid based on whether the color detected by the color sensor corresponds to the color of the specific lid.

14. The blood cell counter of claim 1, wherein a channel resides on the outer surface of the aspirating tube along the longitudinal direction of the aspirating tube, and wherein the channel equalizes the pressure within the sample container with the pressure outside the sample container.

15. The blood cell counter of claim 1, wherein the agitation device includes members that grip the sample container and oscillate the sample container.

16. A blood cell counter comprising:
  a sample aspirator that pierces a lid of a sample container with an aspirating tube and aspirates a whole blood sample in the sample container;
  a detector that counts the blood cells in the whole blood sample aspirated by the aspirator; and
  a force applying member that applies a force to the sample container in an upright state so as to remove the whole blood sample from the lid of the sample container before aspiration by the sample aspirator,
  wherein the force applying member comprises a roller that contacts an outer surface of the sample container and rotates the sample container around an axis parallel to the longitudinal direction of the sample container, and a force applicator that pushes the sample container to the roller while the sample container is rotated, and
  wherein a distance from the outer surface of the roller to the rotational axis of the roller is irregular.

17. A cell counting method comprising:
  mixing a whole blood sample in a sample container by moving the sample container;
  applying a force to a sample container while the sample container is upright to remove whole blood sample attached to the lid of the sample container from the lid,
  wherein applying the force comprises applying a roller that contacts an outer surface of the sample container and rotates the sample container around an axis parallel to the longitudinal direction of the sample container, and applying a force applicator that pushes the sample container to the roller while the sample container is rotated, and
  wherein a distance from an outer circumferential edge of the roller to the rotation center of the roller varies;
  piercing the lid of the sample container with an aspirating tube and aspirating the whole blood sample from the sample container; and
  counting the blood cells contained in the whole blood sample.

18. The cell counting method of claim 17, wherein applying the force to the sample container comprises applying the force so as to move the sample container.

19. The cell counting method of claim 18, wherein applying the force to the sample container comprises applying the force so as to move the sample container in a direction transecting the longitudinal direction of the sample container.

20. The cell counting method of claim 19, further comprising:
  supporting at least a head in the oscillating state, and the sample container in the upright state;
  wherein applying the force to the sample container comprises applying the force in a direction transecting the longitudinal direction of the sample container while the sample container is supported in the sample container supporter.

* * * * *